United States Patent
Frasier et al.

(10) Patent No.: US 7,758,501 B2
(45) Date of Patent: Jul. 20, 2010

(54) SURGICAL REACTORS AND METHODS OF MINIMALLY INVASIVE SURGERY

(75) Inventors: William Frasier, New Bedford, MA (US); Paul Beaudoin, Derry, NH (US)

(73) Assignee: Depuy Spine, Inc., Raynham, MA (US)

( * ) Notice: Subject to any disclaimer, the term of this patent is extended or adjusted under 35 U.S.C. 154(b) by 426 days.

(21) Appl. No.: 11/427,616

(22) Filed: Jun. 29, 2006

(65) Prior Publication Data
US 2007/0156024 A1    Jul. 5, 2007

Related U.S. Application Data

(63) Continuation-in-part of application No. 11/325,620, filed on Jan. 4, 2006.

(51) Int. Cl.
*A61B 1/32* (2006.01)
(52) U.S. Cl. ....................... 600/233; 600/231
(58) Field of Classification Search ........... 600/224, 600/214, 233, 219, 201, 210, 220, 222, 231; 606/198
See application file for complete search history.

(56) References Cited

U.S. PATENT DOCUMENTS

| | | | |
|---|---|---|---|
| 447,761 A * | 3/1891 | Clough | 600/224 |
| 475,975 A * | 5/1892 | Clough | 600/224 |
| 563,236 A | 6/1896 | Penhall | |
| 2,053,868 A | 9/1936 | Grosso | |
| 2,320,709 A | 6/1943 | Arnesen | |
| 3,246,646 A | 4/1966 | Murphy Jr. | |
| 3,486,505 A | 12/1969 | Morrison | |
| 3,522,799 A * | 8/1970 | Gauthier | 600/215 |
| 3,771,518 A | 11/1973 | Greissing | |
| 3,848,601 A | 11/1974 | Ma | |
| 3,965,890 A | 6/1976 | Gauthier | |
| 4,010,741 A | 3/1977 | Gauthier | |
| 4,130,113 A | 12/1978 | Graham | |
| 4,156,424 A * | 5/1979 | Burgin | 600/213 |
| 4,254,763 A | 3/1981 | McCready | |
| 4,263,899 A | 4/1981 | Burgin | |
| 4,274,398 A | 6/1981 | Scott | |
| 4,421,107 A | 12/1983 | Estes | |
| 4,434,791 A | 3/1984 | Darnell | |
| 4,545,374 A | 10/1985 | Jacobsen | |
| 4,562,832 A | 1/1986 | Wilder | |

(Continued)

FOREIGN PATENT DOCUMENTS

EP    1090586    4/2001

(Continued)

OTHER PUBLICATIONS

Mayer, H.M. MD., "A New Microsurgical Technique for Minimally Invasive Anterior Lumbar Interbody Fusuon"; Spine; vol. 22(6); 1997; pp. 691-700.

*Primary Examiner*—Thomas C Barrett
*Assistant Examiner*—Christine L Nelson

(57) ABSTRACT

A surgical retractor includes a plurality of blade assemblies interconnected by a plurality of racks. One or more of the blade assemblies is movable along a rack to selectively expand the retractor. At least one of the blade assemblies includes a blade that is rotatably connected to the blade assembly and that is rotatable independent of other blades of the retractor.

16 Claims, 22 Drawing Sheets

U.S. PATENT DOCUMENTS

| | | | |
|---|---|---|---|
| 4,573,448 A | 3/1986 | Kambin | |
| 4,686,966 A | 8/1987 | Tsai | |
| 4,765,311 A | 8/1988 | Kulik | |
| 4,817,587 A | 4/1989 | Janese | |
| 4,862,891 A | 9/1989 | Smith | |
| 4,872,451 A | 10/1989 | Moore | |
| 4,907,132 A | 3/1990 | Parker | |
| 4,934,352 A | 6/1990 | Sullivan, Jr. | |
| 5,000,163 A | 3/1991 | Ray | |
| 5,052,373 A * | 10/1991 | Michelson | 600/217 |
| 5,125,396 A | 6/1992 | Ray | |
| 5,135,525 A | 8/1992 | Biscoping | |
| 5,158,543 A | 10/1992 | Lazarus | |
| 5,171,279 A | 12/1992 | Mathews | |
| 5,231,973 A | 8/1993 | Dickie | |
| 5,231,974 A * | 8/1993 | Giglio et al. | 600/206 |
| 5,242,443 A | 9/1993 | Kambin | |
| 5,279,567 A | 1/1994 | Ciaglia | |
| 5,284,129 A | 2/1994 | Agbodoe | |
| 5,292,309 A | 3/1994 | Van Tassel | |
| 5,304,183 A | 4/1994 | Gourlay | |
| 5,312,360 A | 5/1994 | Behl | |
| 5,342,384 A | 8/1994 | Sugarbaker | |
| 5,375,481 A * | 12/1994 | Cabrera et al. | 74/577 M |
| 5,400,774 A * | 3/1995 | Villalta et al. | 600/224 |
| 5,415,666 A | 5/1995 | Gourlay | |
| 5,429,121 A | 7/1995 | Gadelius | |
| 5,439,464 A | 8/1995 | Shapiro | |
| 5,472,426 A | 12/1995 | Bonati | |
| 5,493,464 A | 2/1996 | Koshikawa | |
| 5,503,617 A | 4/1996 | Jako | |
| 5,509,893 A | 4/1996 | Pracas | |
| 5,520,610 A * | 5/1996 | Giglio et al. | 600/233 |
| 5,554,101 A | 9/1996 | Matula | |
| 5,569,248 A | 10/1996 | Mathews | |
| 5,667,481 A | 9/1997 | Villalta | |
| 5,681,265 A | 10/1997 | Maeda | |
| 5,702,177 A | 12/1997 | Lin | |
| 5,728,046 A | 3/1998 | Mayer | |
| 5,728,097 A | 3/1998 | Mathews | |
| 5,746,720 A | 5/1998 | Stouder | |
| 5,755,660 A | 5/1998 | Tyagi | |
| 5,762,629 A | 6/1998 | Kambin | |
| 5,769,782 A | 6/1998 | Phan | |
| 5,792,044 A | 8/1998 | Foley | |
| 5,810,721 A | 9/1998 | Mueller | |
| 5,813,978 A | 9/1998 | Jako | |
| 5,816,257 A | 10/1998 | Chin | |
| 5,875,782 A | 3/1999 | Ferrari | |
| 5,879,291 A | 3/1999 | Kolata | |
| 5,882,344 A | 3/1999 | Stouder | |
| 5,891,147 A | 4/1999 | Moskovitz | |
| 5,893,831 A | 4/1999 | Koros | |
| 5,897,490 A | 4/1999 | Fox | |
| 5,899,901 A | 5/1999 | Middleton | |
| 5,902,231 A | 5/1999 | Foley | |
| 5,902,233 A * | 5/1999 | Farley et al. | 600/213 |
| 5,902,315 A | 5/1999 | Dubois | |
| 5,928,139 A | 7/1999 | Koros | |
| 5,931,777 A | 8/1999 | Sava | |
| 5,944,658 A * | 8/1999 | Koros et al. | 600/232 |
| 5,947,896 A | 9/1999 | Sherts | |
| 5,954,635 A | 9/1999 | Foley | |
| 5,967,970 A | 10/1999 | Cowan | |
| 5,967,972 A | 10/1999 | Santilli | |
| 5,967,973 A | 10/1999 | Sherts | |
| 5,968,098 A | 10/1999 | Winslow | |
| 5,976,146 A | 11/1999 | Ogawa | |
| 5,981,147 A | 11/1999 | Hallock | |
| 5,984,867 A | 11/1999 | Deckman | |
| 6,030,340 A | 2/2000 | Maffei | |
| 6,033,406 A | 3/2000 | Mathews | |
| 6,042,542 A | 3/2000 | Koros | |
| 6,048,309 A | 4/2000 | Flom | |
| 6,063,088 A | 5/2000 | Winslow | |
| 6,074,343 A | 6/2000 | Nathanson | |
| 6,083,154 A | 7/2000 | Liu | |
| 6,090,043 A | 7/2000 | Austin | |
| 6,090,113 A | 7/2000 | Le Couedic | |
| 6,120,434 A | 9/2000 | Kimura | |
| 6,139,493 A * | 10/2000 | Koros et al. | 600/215 |
| 6,142,935 A | 11/2000 | Flom | |
| 6,152,871 A | 11/2000 | Foley | |
| 6,159,179 A | 12/2000 | Simonson | |
| 6,162,170 A | 12/2000 | Foley | |
| 6,176,823 B1 | 1/2001 | Foley | |
| 6,187,000 B1 | 2/2001 | Davison | |
| 6,197,002 B1 | 3/2001 | Peterson | |
| 6,200,263 B1 | 3/2001 | Person | |
| 6,206,822 B1 | 3/2001 | Foley | |
| 6,206,862 B1 | 3/2001 | Giamanco | |
| 6,217,509 B1 | 4/2001 | Foley | |
| 6,224,545 B1 | 5/2001 | Cocchia | |
| 6,224,608 B1 | 5/2001 | Ciccolella | |
| 6,241,659 B1 | 6/2001 | Bookwalter | |
| 6,261,295 B1 | 7/2001 | Nicholson | |
| 6,264,650 B1 | 7/2001 | Hovda | |
| 6,267,763 B1 | 7/2001 | Castro | |
| 6,277,094 B1 | 8/2001 | Schendel | |
| 6,306,170 B2 | 10/2001 | Ray | |
| 6,322,500 B1 | 11/2001 | Sikora | |
| 6,331,157 B2 | 12/2001 | Hancock | |
| 6,342,036 B1 | 1/2002 | Cooper | |
| 6,371,959 B1 | 4/2002 | Trice | |
| 6,371,968 B1 | 4/2002 | Kogasaka | |
| 6,395,007 B1 | 5/2002 | Bhatnagar | |
| 6,416,465 B2 | 7/2002 | Brau | |
| 6,416,468 B2 | 7/2002 | Deckman | |
| 6,427,034 B1 | 7/2002 | Meis | |
| 6,431,025 B1 * | 8/2002 | Koros et al. | 74/577 M |
| 6,461,330 B1 | 10/2002 | Miyagi | |
| 6,464,634 B1 | 10/2002 | Fraser | |
| 6,468,207 B1 | 10/2002 | Fowler | |
| 6,520,907 B1 | 2/2003 | Foley | |
| 6,527,466 B1 | 3/2003 | Blier | |
| 6,530,880 B2 | 3/2003 | Pagliuca | |
| 6,530,883 B2 | 3/2003 | Bookwalter | |
| 6,530,926 B1 | 3/2003 | Davison | |
| 6,537,212 B2 | 3/2003 | Sherts | |
| 6,592,582 B2 | 7/2003 | Hess | |
| 6,599,292 B1 | 7/2003 | Ray | |
| 6,616,605 B2 | 9/2003 | Wright | |
| 6,639,965 B1 | 10/2003 | Hsieh | |
| 6,656,176 B2 | 12/2003 | Hess | |
| 6,659,945 B2 | 12/2003 | Ball | |
| 6,679,833 B2 | 1/2004 | Smith | |
| 6,689,054 B2 | 2/2004 | Furnish | |
| 6,692,434 B2 | 2/2004 | Ritland | |
| 6,712,825 B2 | 3/2004 | Aebi | |
| 6,716,218 B2 | 4/2004 | Holmes | |
| 6,723,043 B2 | 4/2004 | Kleeman | |
| 6,729,205 B2 | 5/2004 | Phillips | |
| 6,733,445 B2 | 5/2004 | Sherts et al. | |
| 6,740,102 B2 | 5/2004 | Hess | |
| 6,755,839 B2 | 6/2004 | Van Hoeck | |
| 6,764,444 B2 | 7/2004 | Wu | |
| 6,793,656 B1 | 9/2004 | Mathews | |
| 6,814,700 B1 | 11/2004 | Mueller | |
| 6,869,398 B2 | 3/2005 | Obenchain | |
| 6,893,394 B2 | 5/2005 | Douglas et al. | |
| 6,896,680 B2 | 5/2005 | Michelson | |
| 6,939,297 B2 | 9/2005 | Gannoe | |
| 6,945,933 B2 | 9/2005 | Branch | |
| 6,982,740 B2 | 1/2006 | Adair | |

| | | | | | |
|---|---|---|---|---|---|
| 7,008,432 B2 | 3/2006 | Schlapfer | 2005/0159650 A1 * | 7/2005 | Raymond et al. ............ 600/201 |
| 7,052,497 B2 | 5/2006 | Sherman | 2005/0159651 A1 * | 7/2005 | Raymond et al. ............ 600/213 |
| 7,074,226 B2 | 7/2006 | Roehm | 2005/0171551 A1 | 8/2005 | Sukovich |
| 7,081,118 B2 | 7/2006 | Weber | 2005/0215866 A1 | 9/2005 | Kim |
| 7,087,055 B2 | 8/2006 | Lim | 2006/0074278 A1 | 4/2006 | Petit |
| 7,097,647 B2 | 8/2006 | Segler | 2006/0084844 A1 | 4/2006 | Nehls |
| 7,150,714 B2 | 12/2006 | Myles | 2006/0195017 A1 | 8/2006 | Shluzas |
| 7,156,085 B2 | 1/2007 | Lewis | 2006/0207612 A1 | 9/2006 | Jackson |
| 7,179,225 B2 | 2/2007 | Shluzas | 2006/0224044 A1 | 10/2006 | Marchek |
| 7,179,261 B2 | 2/2007 | Sicvol | 2006/0247651 A1 | 11/2006 | Roehm |
| 7,198,598 B2 | 4/2007 | Smith | 2007/0038033 A1 * | 2/2007 | Jones et al. ................ 600/219 |
| 7,207,949 B2 * | 4/2007 | Miles et al. ................ 600/554 | 2007/0106123 A1 | 5/2007 | Gorek |
| 7,223,233 B2 | 5/2007 | Branch | 2007/0156023 A1 | 7/2007 | Frasier |
| 7,250,052 B2 | 7/2007 | Landry | 2007/0156024 A1 | 7/2007 | Frasier |
| 7,261,688 B2 | 8/2007 | Smith | 2007/0156025 A1 | 7/2007 | Marchek |
| 7,264,589 B2 | 9/2007 | Sharratt | 2007/0156026 A1 | 7/2007 | Frasier |
| 7,491,168 B2 * | 2/2009 | Raymond et al. ........... 600/231 | 2007/0208228 A1 | 9/2007 | Pavento |
| 7,556,601 B2 | 7/2009 | Branch | 2008/0021285 A1 | 1/2008 | Drzyzga |
| 2001/0029377 A1 | 10/2001 | Aebi | 2009/0018399 A1 * | 1/2009 | Martinelli et al. ........... 600/210 |
| 2002/0002324 A1 | 1/2002 | McManus | | | |
| 2002/0058948 A1 | 5/2002 | Arlettaz | | | |

FOREIGN PATENT DOCUMENTS

| | | |
|---|---|---|
| EP | 1192905 | 4/2002 |
| FR | 2807313 | 10/2001 |
| WO | 0180725 | 11/2001 |
| WO | 2005096735 | 10/2005 |
| WO | WO 2005096735 A2 * | 10/2005 |

| | | | |
|---|---|---|---|
| 2003/0149341 A1 | 8/2003 | Clifton | |
| 2003/0220650 A1 | 11/2003 | Major | |
| 2004/0230191 A1 | 11/2004 | Frey | |
| 2004/0242969 A1 | 12/2004 | Sherts | |
| 2005/0043592 A1 | 2/2005 | Boyd | |
| 2005/0131422 A1 | 6/2005 | Anderson | |
| 2005/0137461 A1 * | 6/2005 | Marchek et al. ............ 600/220 |

* cited by examiner

SURGICAL REACTORS AND METHODS OF MINIMALLY INVASIVE SURGERY

REFERENCE TO RELATED APPLICATION

This application is a continuation-in-part of U.S. patent application Ser. No. 11/325,620, filed Jan. 4, 2006, which is hereby incorporated by reference.

BACKGROUND

In surgical procedures, it is important to minimize trauma to the patient and damage to tissue to facilitate patient recovery. One way to accomplish this is to minimize the size of the incision for the surgical procedure and minimize the cutting of tissue to access the target anatomy. A number of retractors are available that are designed to expand a small surgical incision and provide access to a surgical site. Such retractors typically include two or more retractor blades that separate to expand the incision and create an access channel through which to conduct the surgical procedure. One problem with such retractors is that the access channel of the expanded retractor is often restricted to one shape or configuration.

SUMMARY

Disclosed herein are surgical retractors and methods of minimally invasive surgery that minimize tissue trauma and facilitate access to a surgical site. In one exemplary embodiment, a surgical retractor comprises a plurality of blade assemblies interconnected by a plurality of racks. One or more of the blade assemblies may be movable along a rack to selectively expand the retractor. At least one of the blade assemblies includes a blade that is rotatably connected to the blade assembly and that may be rotatable independent of other blades of the retractor.

In another exemplary embodiment, a surgical retractor may comprise a first blade assembly having a first blade and second blade connected thereto and a second blade assembly having a third blade and a fourth blade connected thereto. The first blade assembly may be connected by a first rack to the second blade assembly and at least one of the first blade assembly and the second blade assembly may be movable along the first rack relative. The first blade assembly may be connected by a second rack to the second blade assembly and at least one of the first blade assembly and the second blade assembly may be movable along the second rack. The retractor may be adjustable between a closed configuration in which the first blade assembly and second blade assembly are proximate one another at at least the proximal end thereof and an expanded configuration in which the first blade assembly and the second blade assembly are displaced from another. The first blade may be rotatably connected to the first blade assembly and may be rotatable independent of the second blade relative to the first blade assembly. The second blade may be rotatably connected to the second blade assembly and may be rotatable independent of the first blade relative to the second blade assembly. The retractor may further include a gear positioned in the first blade assembly engaging the first rack to facilitate movement of the first blade assembly relative to the second blade assembly.

In accordance with another exemplary embodiment, a kit for accessing a surgical site may comprise a surgical retractor including a plurality of blade assemblies interconnected by a plurality of racks and an instrument for moving one or more of the blade assemblies along the rack and rotating at least one of the blades with respect to the assemly. One or more of the blade assemblies may be movable along a rack to selectively expand the retractor, at least one of the blade assemblies includes a blade rotatably connected to the blade assembly and rotatable independent of other blades of the retractor. The instrument may engage an internal or external drive feature to move the blade assemblies along the rack or to rotate the blade connected to the blade assembly.

BRIEF DESCRIPTION OF THE FIGURES

These and other features and advantages of the surgical retractors and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

DETAILED DESCRIPTION OF EXEMPLARY EMBODIMENTS

Figure 1:
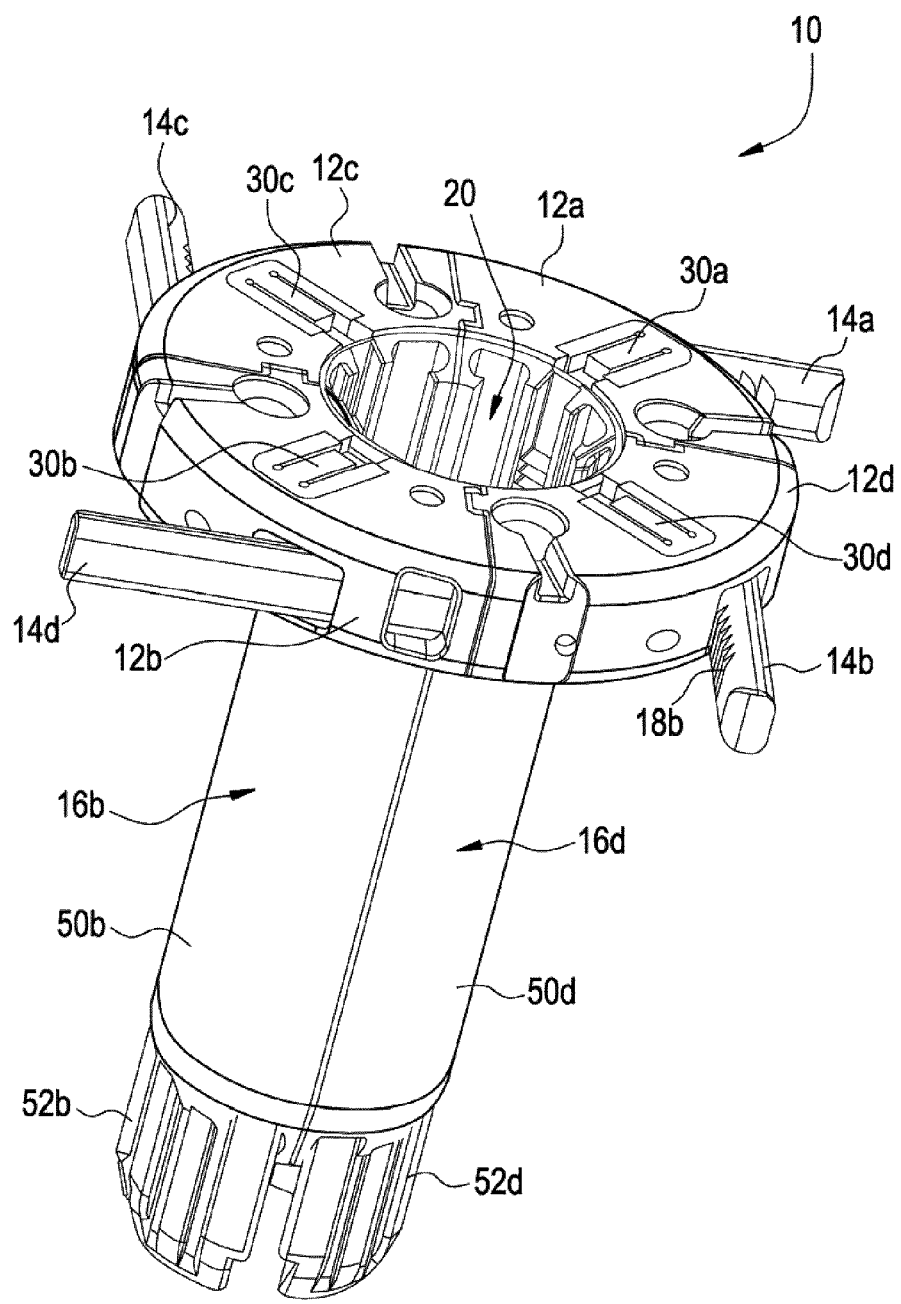
FIG. 1 is a perspective view of an exemplary embodiment of a surgical retractor, illustrating the retractor in a closed configuration.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-8 illustrate an exemplary embodiment of a surgical retractor 10 suitable for providing a selectively expandable access channel through which a surgical procedure may be performed on target anatomy. The exemplary surgical retractor is particularly suited for minimally invasive spine surgery and, to this end, may be inserted through a relatively small incision to provide a selectively expandable access channel from the skin to the target spinal anatomy. The exemplary surgical retractor 10 includes a plurality of blade assemblies 12 interconnected by a plurality of racks 14 allowing one or more of the blade assemblies 12 to be displaced along a rack to selectively expand the access channel. The blade assemblies 12 include tissue engaging blades 16, some or all of which may be independently rotated to allow the access channel of the retractor 10 to be selectively expanded into a variety of different shapes and sizes.

The surgical retractors disclosed herein may include a plurality of blade assemblies 12 that may include tissue engaging blades 16 that define an access channel 20 for the retractor. Any number of blade assemblies 12 may be provided. For example, a surgical retractor may include two blade assemblies, three blade assemblies, or four blade assemblies. The number (and size and shape) of blade assemblies may vary depending on, for example, the size and shape of the access channel desired, the procedure being performed, and the surgical approach, e.g. posterior, anterior, or lateral. The illustrated exemplary surgical retractor 10 includes four blade assemblies: first blade assembly 12a, second blade assembly 12b, third blade assembly 12c, and fourth blade assembly 12d.

The blade assemblies 12 of the retractors disclosed herein may be interconnected by a number of racks 14 that allow selective displacement of the blade assemblies from one another to expand the access channel of the retractor. The number of racks 14 provided can vary depending on, for example, the desired expansion of the access channel. In the illustrated embodiment, the retractor 10 includes four racks: first rack 14a, second rack 14b, third rack 14c, and fourth rack 14d. In particular, the first blade assembly 12a may be connected by the first rack 14a to the third blade assembly 12c and the first blade assembly 12a may be movable along the first rack 14a relative to the third blade assembly 12c. The first blade assembly 12a may be connected by the second rack 14b to the fourth blade assembly 12d and the fourth blade assembly 12d may be movable along the second rack 14b relative to the first blade assembly 12a. The second blade assembly 12b may be connected by the third rack 14c to the third blade assembly 12c and the third blade assembly 12c may be movable along the third rack 14c relative to the second blade assembly 12b. The second blade assembly 12b may be connected by the fourth rack 14d to the fourth blade assembly 12d and the second blade assembly 12b may be movable along the fourth rack 14d relative to the fourth blade assembly 12d.

In another exemplary embodiment, a retractor may include a first blade assembly having a first blade connected thereto and a second blade assembly having a second blade connected thereto. A first rack may connect the first blade assembly and the second blade assembly and the first blade assembly and/or the second blade assembly may be movable along the first rack. A second rack may connect the first blade assembly and the second blade assembly and the first blade assembly and/or the second blade assembly may be movable along the second rack.

The retractors disclosed herein may include a mechanism for selectively locking the position of a blade assembly 12 relative a rack 14. In the illustrated embodiment, for example, the retractor 10 includes a ratchet mechanism for selectively displacing a blade assembly 12 relative to a respective rack 14. Each rack 14a-d includes a plurality of teeth 18a-d extending along the length of the rack 14. Each blade assembly 12a-d includes a complementary pawl that can selectively engage the teeth 18 of a respective rack to lock the position of the blade assembly 12 relative to the rack 14, when the teeth are engaged by the pawl, or to release the blade assembly 12 from the rack 14 to permit motion along the rack 14 when the pawl is disengaged from the rack. One skilled in the art will appreciate that other mechanisms, including, for example, a screw or the like that may be selectively advanced relative to the blade assembly into contact with the respective rack, may be employed to permit selective displacement of a blade assembly relative to a rack.

The shape of a rack 14 along its longitudinal axis can be varied to provide an expanded access channel having a different size and shape. In the illustrated exemplary embodiment, for example, all of the racks 14a-d of the surgical retractor 10 are linear. In such a configuration, the blade assemblies 12a-d may be displaced along a respective rack 14a-d with each blade 16a-d remaining parallel in orientation with respect to the other blades. In alternative embodiments, one or more of the racks 14 may be arcuate along its length to permit lateral and angular expansion of the access channel or may be flexible or hinged allowing for variable angular expansion.

Figure 4:
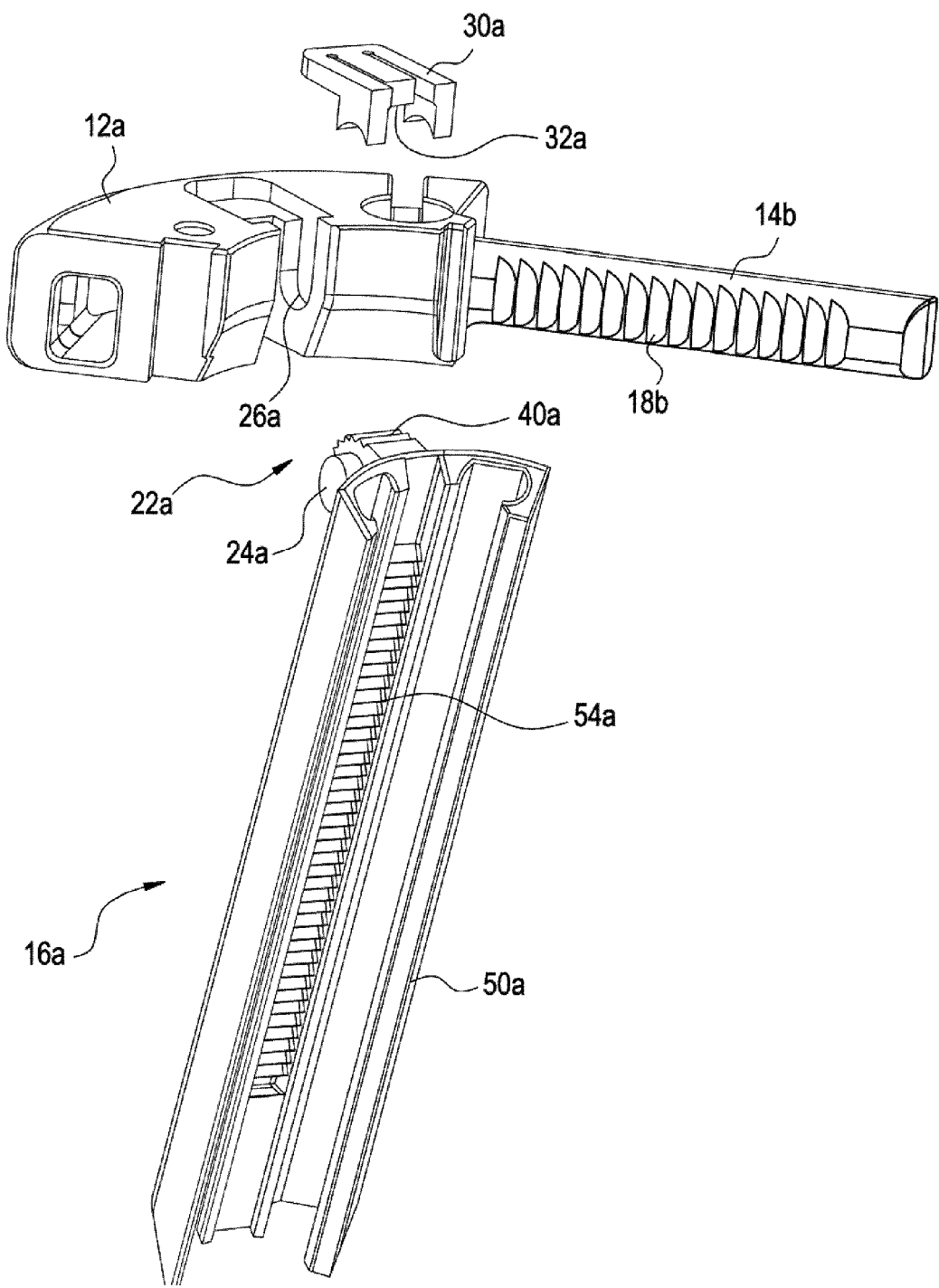
FIG. 4 is an exploded view of an exemplary blade assembly of the retractor of FIG. 1.
Figure 5:
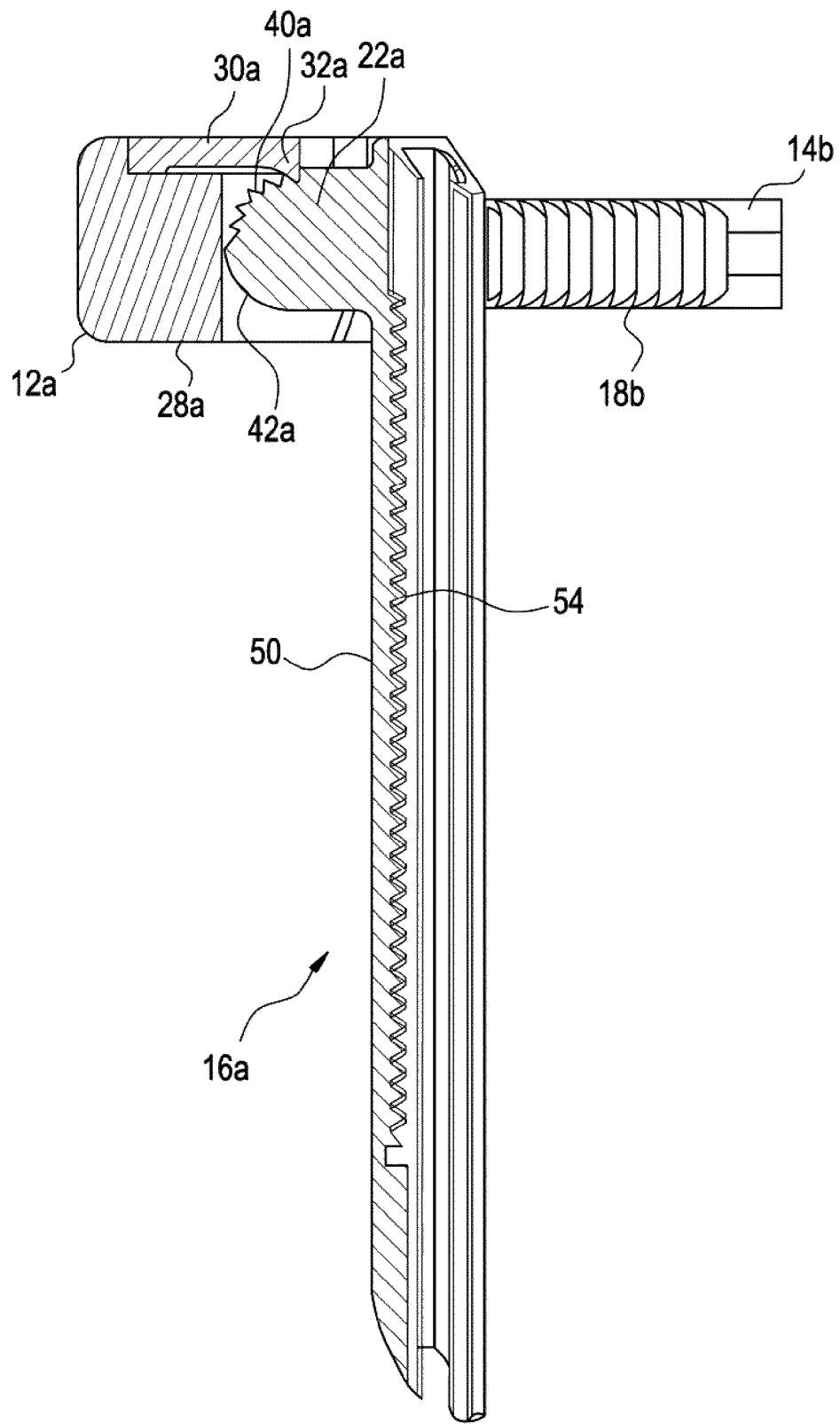
FIG. 5 is a side view in cross section of an exemplary blade assembly of the retractor of FIG. 1, illustrating the blade of the blade assembly in a first, closed position.
Figure 6:
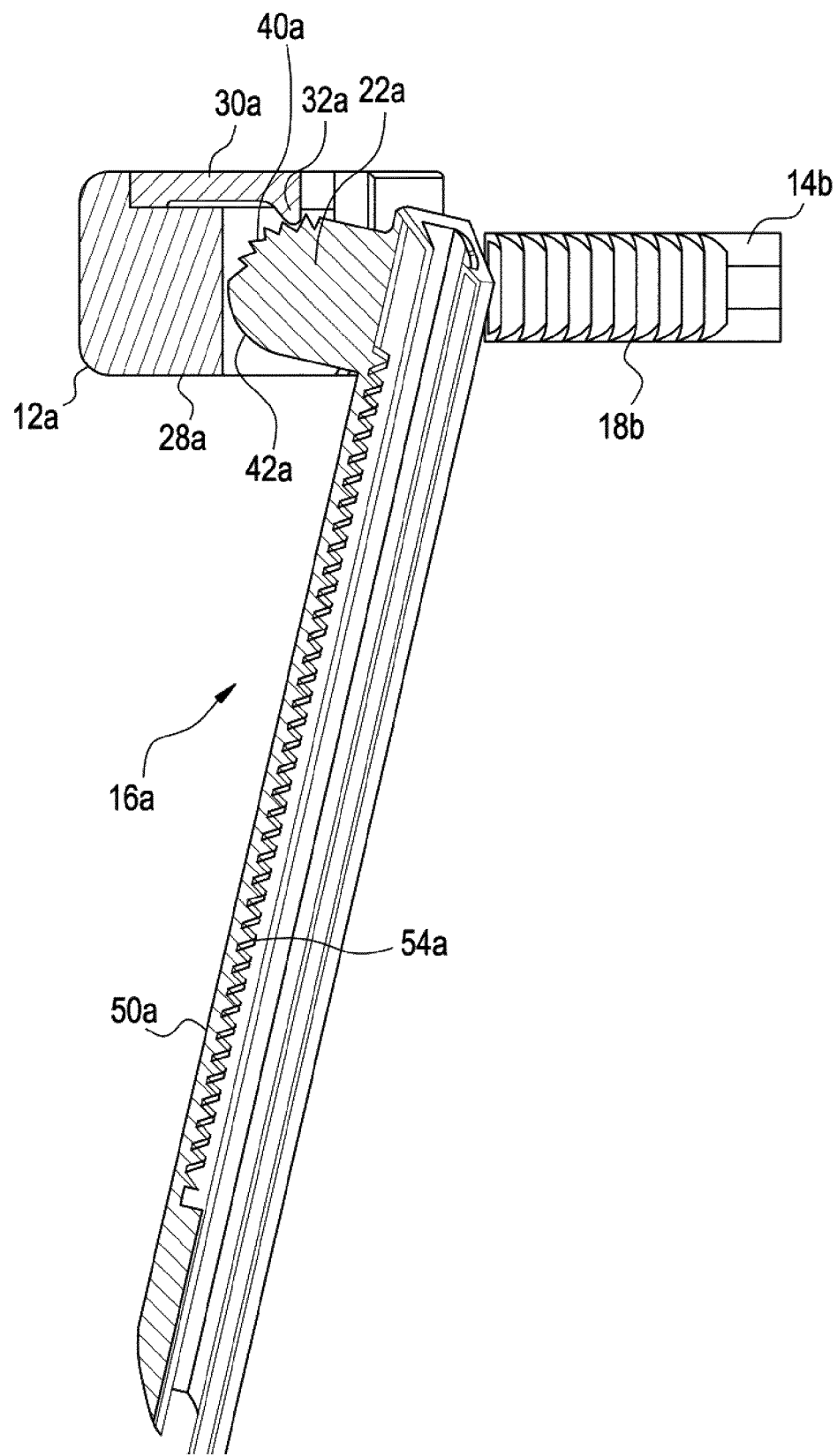
FIG. 6 is a side view in cross section of an exemplary blade assembly of the retractor of FIG. 1, illustrating the blade of the blade assembly in a second, expanded position.

In the exemplary retractors disclosed herein, the blade 16 of one or more of the blade assemblies 12 of the retractor may be rotationally adjustable relative to the blade assembly and the blade 16 may be rotatable independent of other blades of the retractor. For example, a blade 16 may be rotationally connected to the blade assembly. In the exemplary embodiment, the blade assemblies 12a-d each include a blade 16a-d that is rotationally connected to its respective blade assembly. In such a configuration, each blade 16a-d may rotate relative to the respective blade assembly 12a-d independent of the other blades to selectively expand the access channel 20 of the retractor 10. In the illustrated embodiment, the proximal end 22 of each blade 16 can be configured to facilitate rotational connection of the blade 16 to the blade assembly 12. Referring to FIG. 4, for example, the proximal end 22a of the first blade 16a may include an integral rotation shaft 24a that may seat within a pair of grooves 26a provided in the first blade assembly 12a. The rotation shaft 24a of the first blade 16a defines a rotation axis about which the first blade 16a may rotate. In the illustrated embodiment, the rotation axis of the first blade 16a is oriented in plane that is generally parallel to the plane defined by the axis of the first rack 14a and the second rack 14b, as well as the plane defined by the bottom surface 28a of the first blade assembly 12a. The first blade 16a may rotate between a first, closed position, illustrated in FIG. 5, in which the blade 16a is oriented approximately perpendicular to a plane defined by the bottom surface 28a of the blade assembly 12a, and a second, fully expanded position in which the blade 16a is oriented at an angle other than perpendicular to plane defined by the bottom surface 28a of the blade assembly 12a. The first blade 12a may be rotated to any position between the first, closed position and the second, fully expanded position. FIG. 6 illustrates the first blade in an expanded position between the first, closed position and the second, fully expanded configuration. In the illustrated embodiment, the second, third and fourth blade assemblies 12b-d are constructed in a manner analogous to the first blade assembly 12a.

Figure 2:
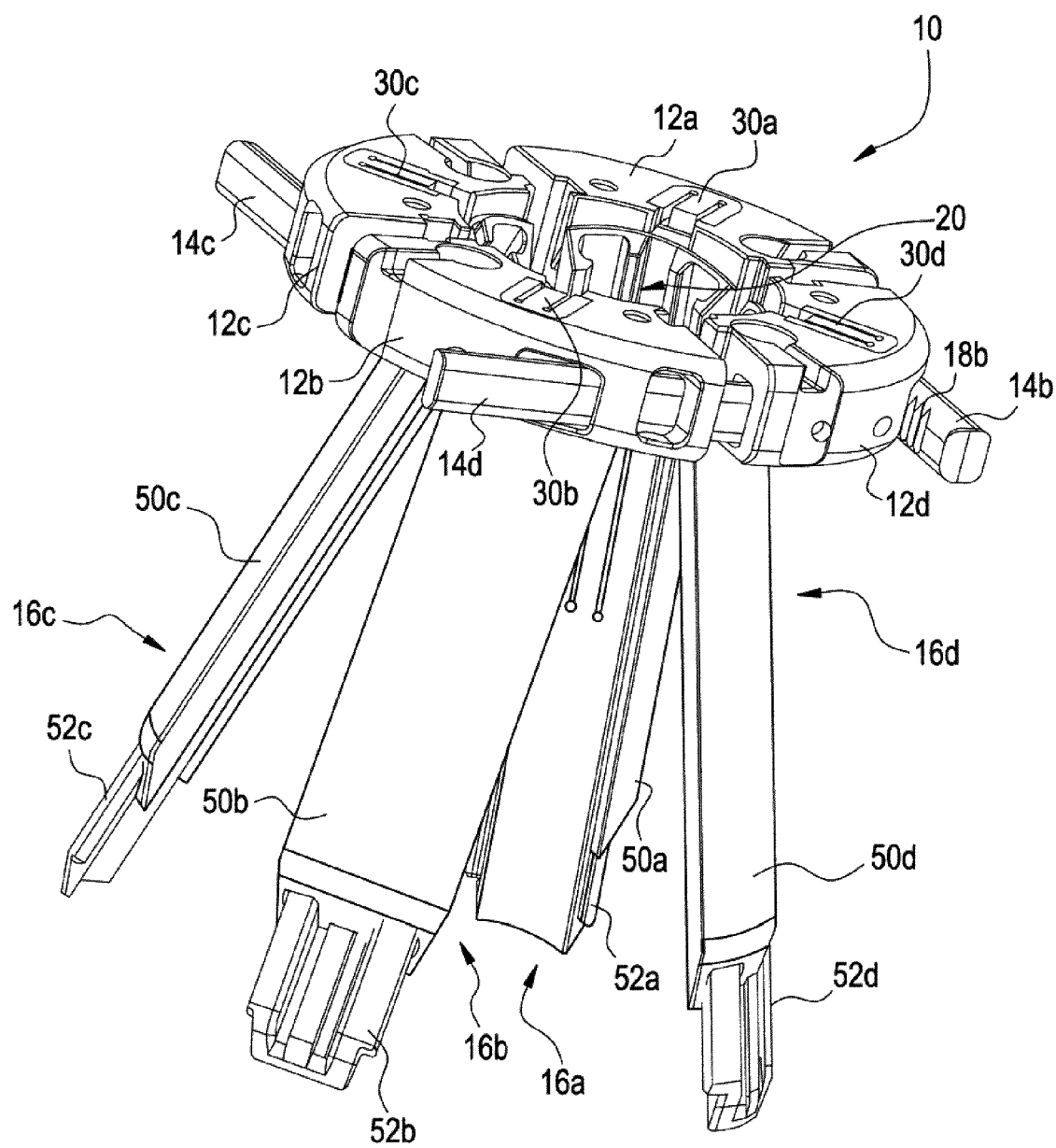
FIG. 2 is a perspective view of the retractor of FIG. 1, illustrating the retractor in an expanded configuration.
Figure 3:
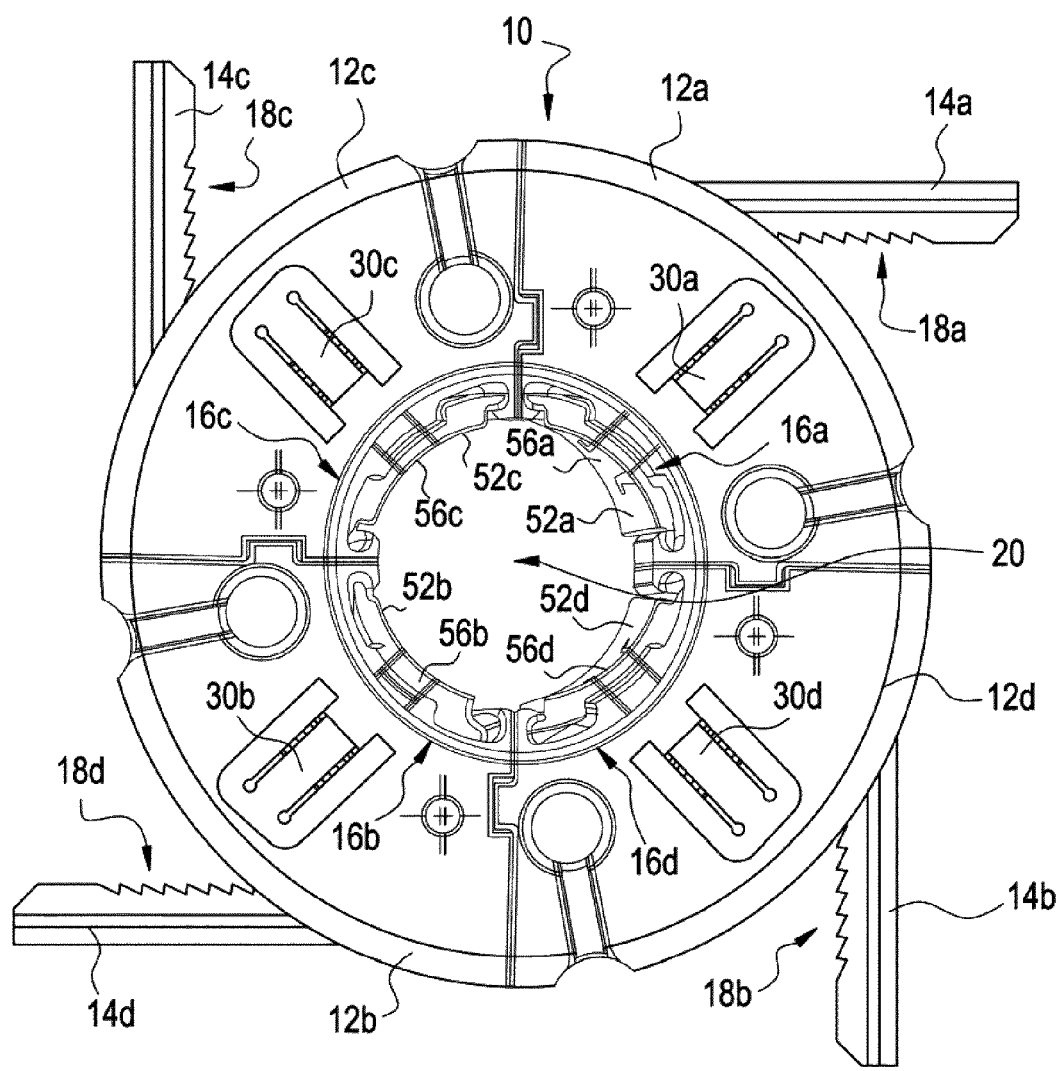
FIG. 3 is a top view of the retractor of FIG. 1, illustrating the retractor in a closed configuration.
Figure 14:
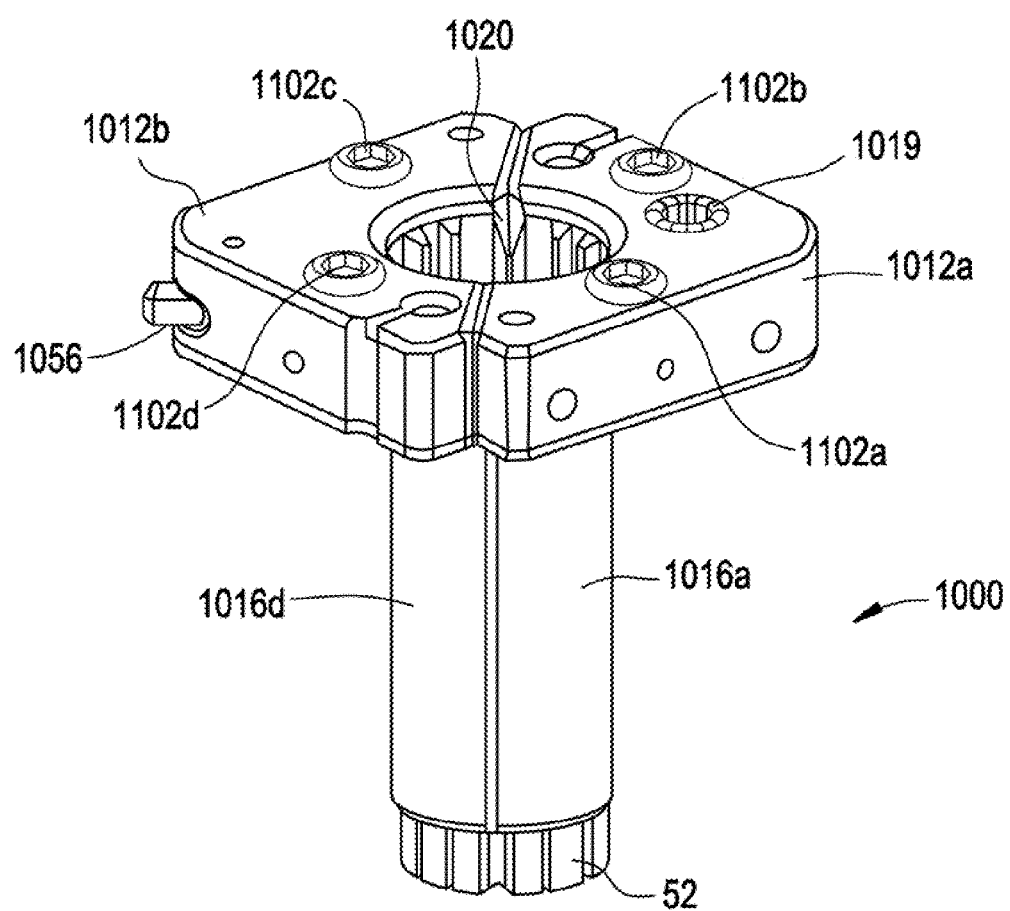
FIG. 14 is a perspective view of an alternative embodiment of a surgical retractor, illustrating the retractor in a closed configuration.
Figure 15:
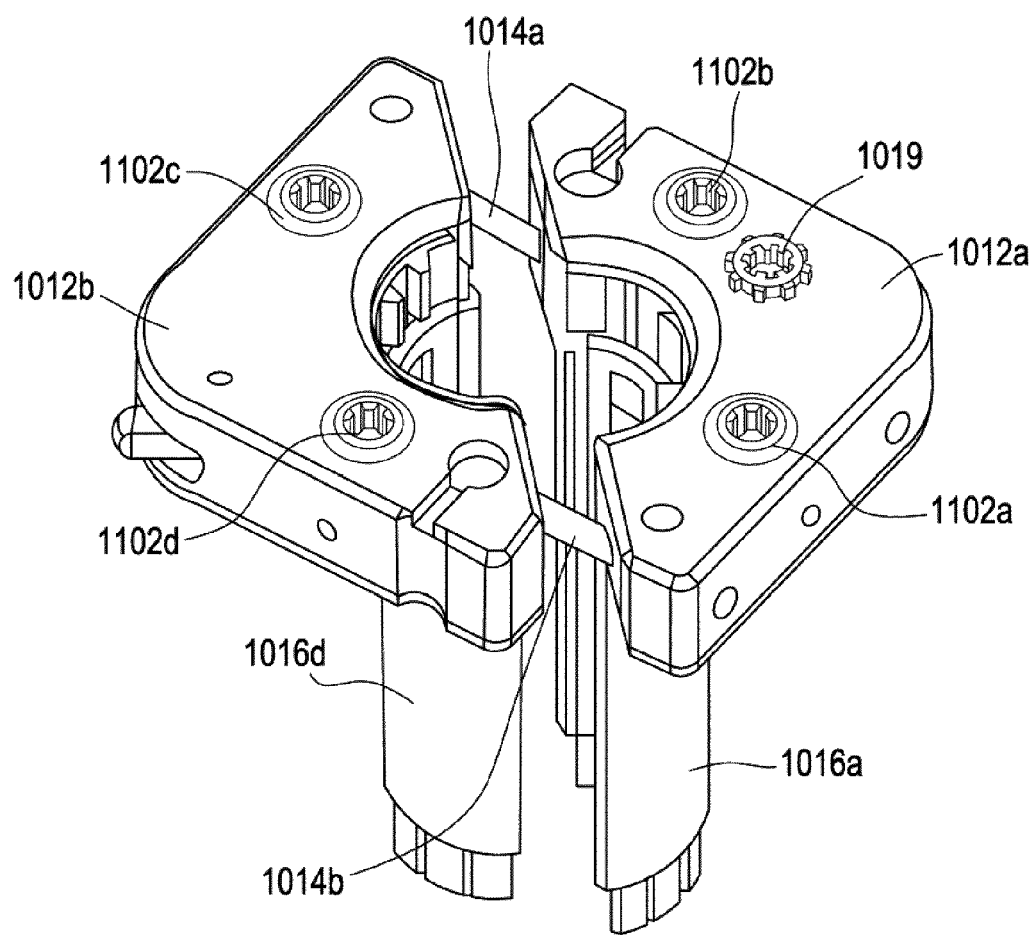
FIG. 15 is a perspective view of the retractor in FIG. 14, illustrating the retractor in an expanded configuration.
Figure 16:
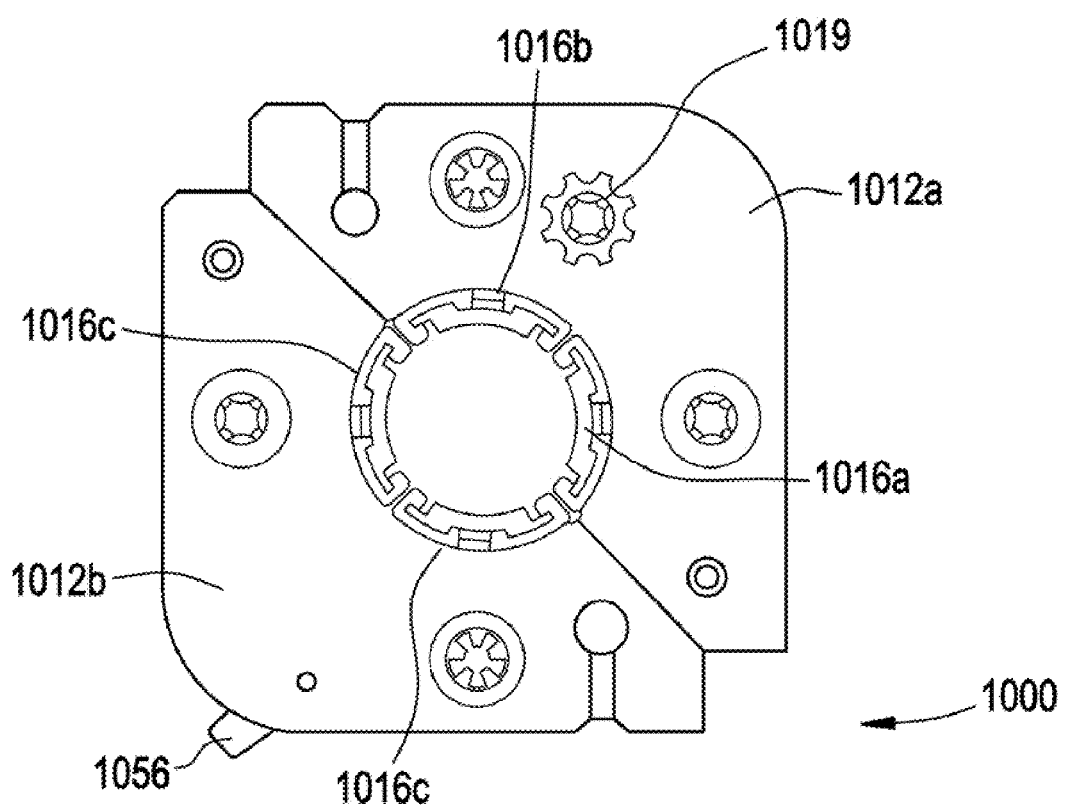
FIG. 16 is a top view of the retractor in FIG. 14, illustrating the retractor in a closed configuration.
Figure 18:
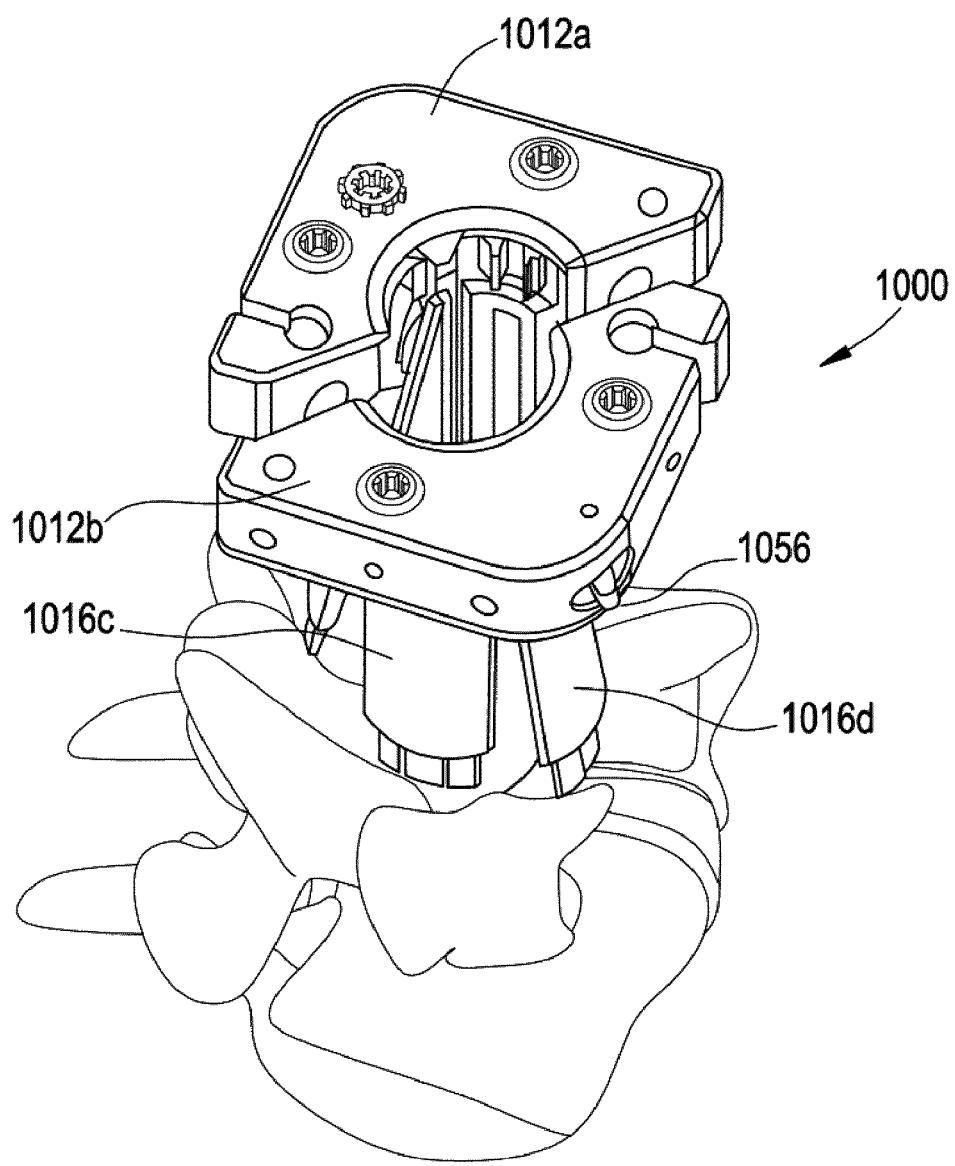
FIG. 18 is a perspective view of the retractor of FIG. 14, illustrating the retractor in an expanded configuration and positioned to provide access to spinal anatomy in a posterior approach.

The retractors disclosed herein may be adjustable between a closed configuration, illustrated in FIGS. 1, 3, and 14 in which the blades 16a-d, 1016a-d of the blade assemblies 12a-d, 1012a-b are proximate or may contact adjacent blades along at least a portion of the length of the blades 16a-d, 1016a-d to form a continuously approximately enclosed access channel 20, 1020 and a fully expanded configuration in which the blade assemblies 12a-d, 1012a-b are fully displaced along a respective rack 14a-d, 1014a-b and the blades 16a-d, 1016a-d are adjusted to the second, fully expanded position. The exemplary retractors 10, 1000 may be expanded to any configuration between the closed configuration and the fully expanded configuration. FIGS. 2 and 18 illustrate the exemplary retractors 10, 1000 in an expanded configuration between the closed configuration and the fully expanded configuration. The cross sectional size and shape of the access channel 20 in the closed configuration may vary depending on, for example, the number of blades provided, the surgical procedure being performed and the designed approach, e.g., anterior, lateral, or posterior. For example, the cross-sectional shape may be oval, rectangular or triangular. In the exemplary embodiment, the blades 16a-d form a cylindrical access channel 20 having a circular cross section when the blades 16a-d are in the first, closed position. The amount of rotational adjustment for the blades 16a-d between the first, closed position and the second, fully expanded position may be varied. For example, in the exemplary embodiment, each blade 16 may rotate approximately 45° between the first, closed position and the second, fully expanded position.

The retractor 10 may include a blade adjustment mechanism for selectively adjusting the rotational position of a rotationally adjustable blade. Referring to the first blade assembly 12a, for example, the blade adjustment mechanism of the exemplary retractor 10 may be a pawl 30a connected to blade assembly 12a for selectively engaging a plurality of teeth 40a provided on the proximal end 22a of a blade 16a. Each blade assembly of the exemplary retractor 10 may include an analogous adjustment mechanism, as in the illustrated retractor 10, or may have distinct blade adjustment mechanisms. Continuing to refer to first blade assembly 16a and FIGS. 4-6, for example, the pawl 30a may be a leaf spring having a tooth 32a for selectively engaging the teeth 40a on the proximal end 22a of the first blade 16a. The tooth 32a of the pawl 30a may pivot into and out of engagement with the teeth 40a provided on the proximal end 22a of the first blade 16a. The tooth 32a of the pawl 30a may be biased into engagement with the teeth 40a of the first blade 16a. The teeth 40a may be provided on an arcuate surface 42a of the proximal end 22a of the first blade 16a to facilitate rotational positioning of the first blade 16a. When the tooth 32a of the pawl 30a is engaged with the teeth 40a of the first blade 16a, the pawl 30a inhibits rotation of the first blade 16a. When the tooth 32a of the pawl 30a is pivoted out of engagement with the teeth 40a, the first blade 16a may be rotated into the desired rotational position.

Figure 9:
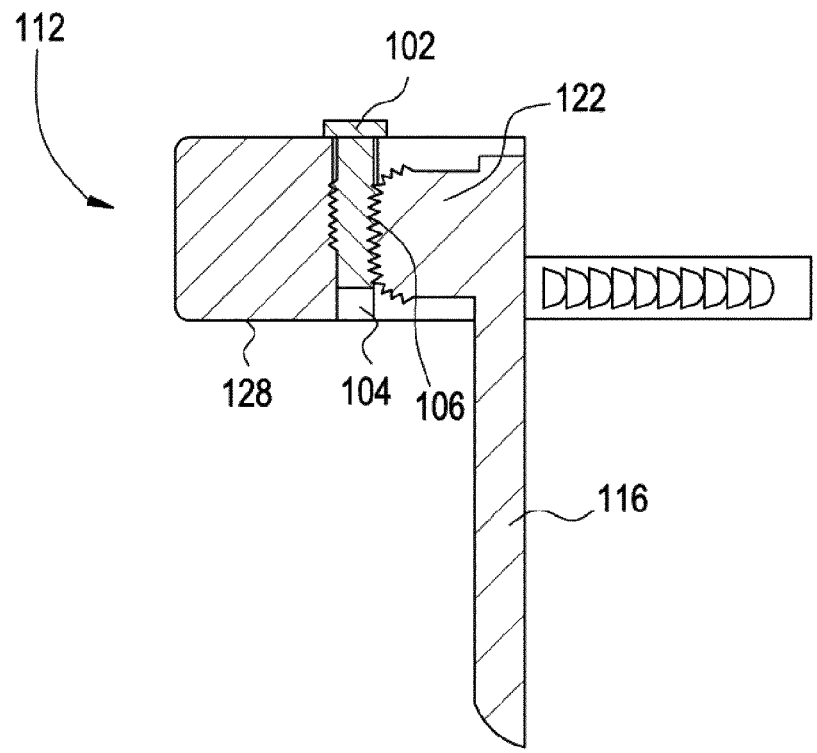
FIG. 9 is a side view in cross section of an alternative embodiment of a blade assembly.

In alternative embodiments, the blade adjustment mechanism may have a different structure. Referring to FIG. 9, for example, the blade adjustment mechanism of an exemplary blade assembly 112 may include a screw 102 received within a threaded hole 104 provided in the blade assembly 112. The threads of the screw 102 engage threads 106 provided on the proximal end 122 of the blade 116. Rotation of the screw 102 relative to the blade 116 can adjust the rotational position of a rotationally adjustable blade 116. In the exemplary embodiment, the axis of the screw 102 is oriented generally perpendicular to the plane defined by the bottom surface 128 of the blade assembly 112. Rotation of the screw 102 in a first direction causes the blade 116 to rotate from a first, closed position, illustrated in FIG. 9, toward a second, fully expanded position. Rotation of the screw 102 in a second direction, opposite the first direction, causes the blade 116 to rotate from an expanded position toward the closed position.

Alternatively, the blade adjustment mechanism may include a screw received within a threaded bushing connected to the first blade. Rotation of the screw may cause the bushing to move along an axis of the screw to adjust the rotational orientation of the first blade.

Figure 10:
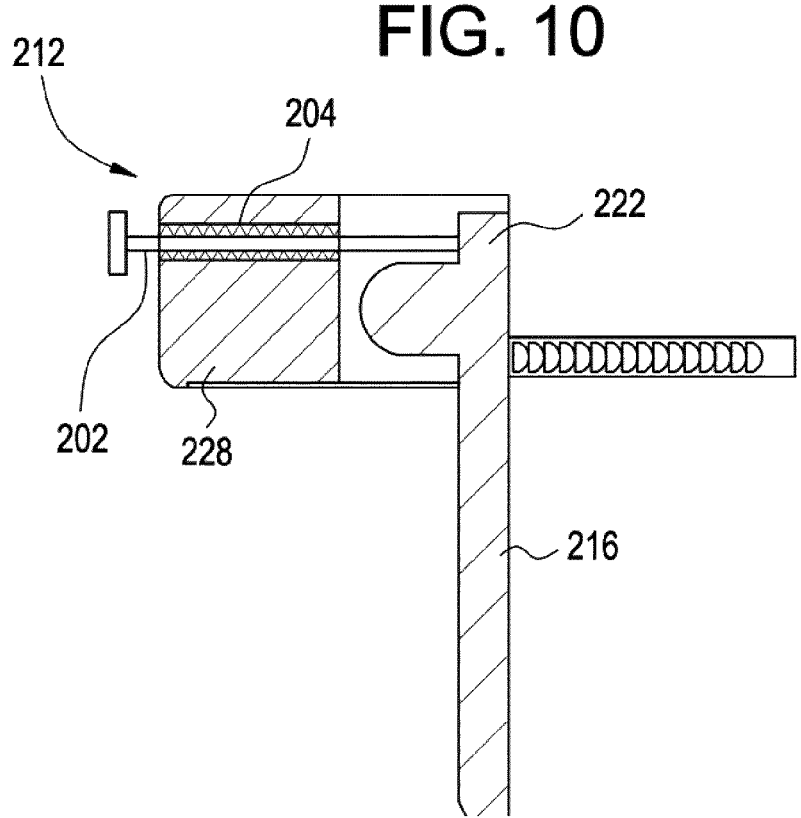
FIG. 10 is a side view in cross section of an alternative embodiment of a blade assembly.

Referring to FIG. 10, another exemplary embodiment of a blade adjustment mechanism is illustrated. The blade adjustment mechanism of the exemplary blade assembly 212 includes a screw 202 received within a threaded hole 204 provided in the blade assembly. The screw 202 has a screw axis that is oriented generally parallel to the plane defined by the bottom surface 228 of the blade assembly. The distal end of the screw 202 may engage the proximal end 222 of the tissue engaging blade 216. Movement of the screw 202 along a screw axis relative to the blade assembly 212 adjusts the rotational orientation of the blade 216 by rotating the blade 216 about the rotation axis of the blade 216.

Figure 11:
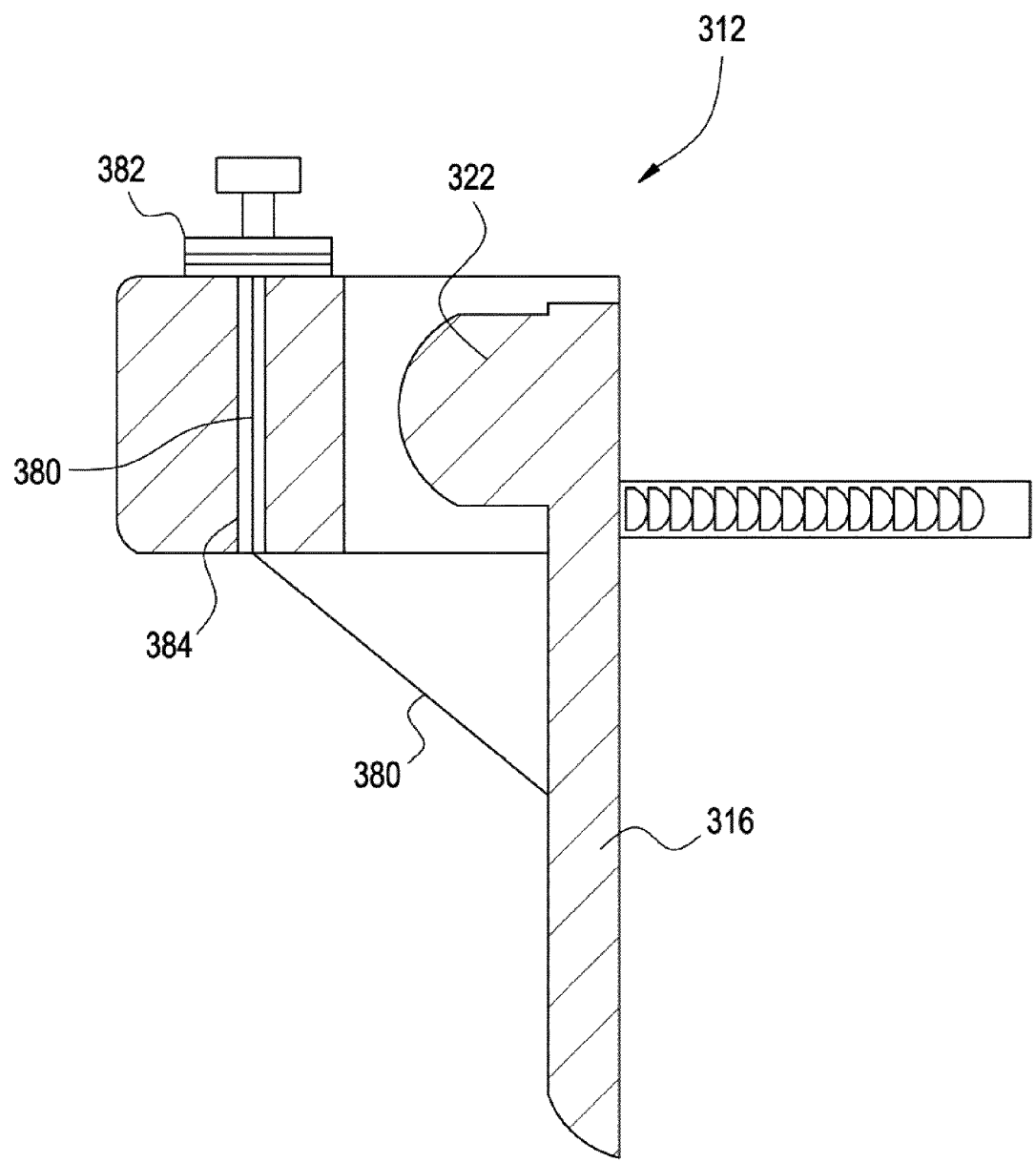
FIG. 11 is a side view in cross section of an alternative embodiment of a blade assembly.

Referring to FIG. 11, another exemplary embodiment of blade adjustment mechanism is illustrated. The blade adjustment mechanism of the exemplary blade assembly 312 includes cable 380 positioned through an opening 384 in the blade assembly 312. The cable 380 may be connected at one end to a tissue engaging blade 316. At the other end, the cable 380 may be connected to a wheel 382 about which the cable 380 may be wound. Adjustment of the cable 380 along the axis of the cable 380 adjusts the rotational position of the blade 316. Rotation of the wheel 382 can cause the cable 380 to pull on the blade 316 and rotate the blade 316 about the shaft 322. A spring may be provided to bias the blade 316 to the first, closed position illustrated in FIG. 11.

Figure 12:
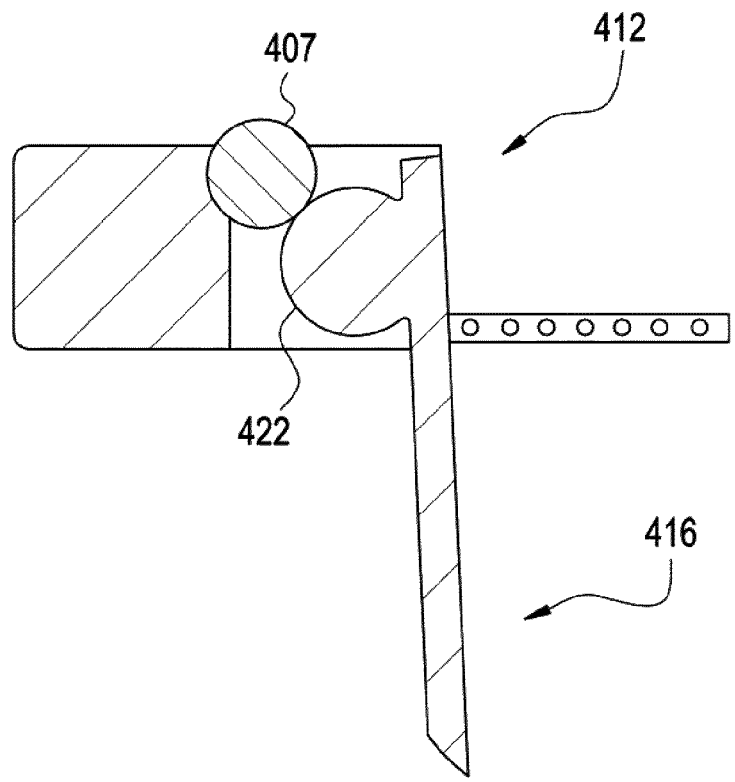
FIG. 12 is a side view in cross section of an alternative embodiment of a blade assembly.

Referring to FIG. 12, another exemplary embodiment of a blade adjustment mechanism is illustrated. The blade adjustment mechanism of the exemplary blade assembly 412 includes a rotatable disk 407 rotatably connected to the blade assembly 412 and engageable with the proximal end 422 of the tissue engaging blade 416. In the exemplary embodiment, the proximal end 422 of the blade 416 includes an arcuate surface for engaging the disk 407. Rotation of the disk 407 relative to the blade assembly 412 rotates the proximal end 422 of the blade 416 to adjust the rotational orientation of the blade 416. In certain exemplary embodiments, the disk 407 may be a gear having teeth for engaging teeth provided on the arcuate surface of the proximal end 422 of the blade 416.

Figure 13:
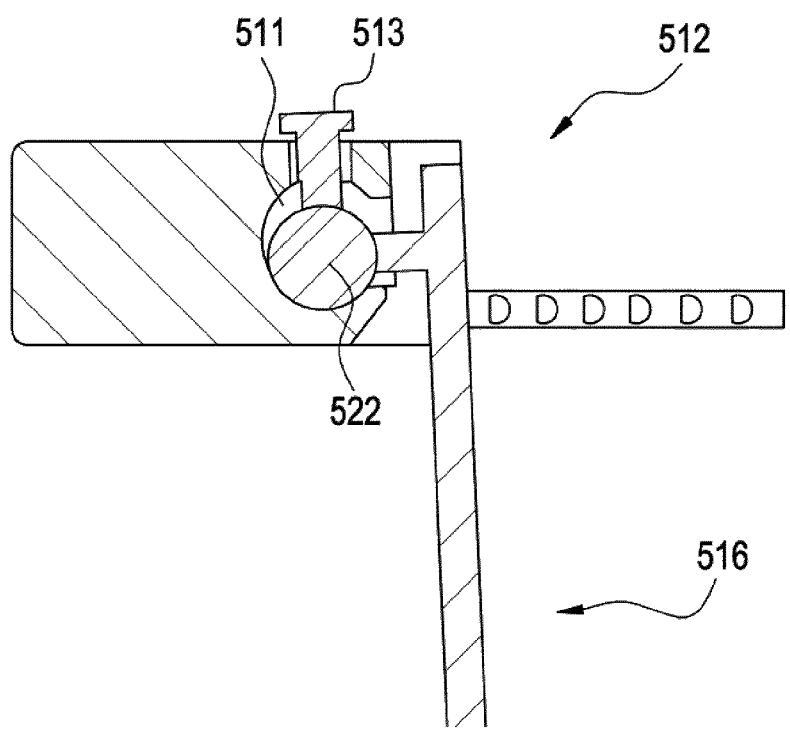
FIG. 13 is a side view in cross section of an alternative embodiment of a blade assembly.

Referring to FIG. 13, another exemplary embodiment of a blade adjustment mechanism is illustrated. The blade adjustment mechanism of the exemplary blade assembly 512 includes a cavity 511 provided in the blade assembly 512 for receiving the proximal end 522 of a tissue engaging blade 516. In the exemplary embodiment, the cavity 511 has a size and shape complementary to the size and shape of the proximal end 522 of the blade 516 and selected to allow the blade 516 to rotate relative to the blade assembly 512. In the exemplary embodiment, for example, the proximal end 522 of the blade 516 may be approximately spherical in shape and the cavity 511 may include a seat that is approximately spherical in shape for engaging the proximal end 522 of the blade 516. A screw 513 or the like may be provided to fix the proximal end 522 of the blade 516 into contact with the seat of the cavity 511 and thereby inhibit rotation of the blade 516.

One skilled in the art will appreciate that other blade adjustment mechanisms may be employed to adjust the rotational position of a rotationally adjustable blade.

In an alternate exemplary embodiment, the retractor 1000 may include two blade assemblies. As illustrated in FIGS. 14-24, the retractor 1000 has a first blade assembly 1012a and a second blade assembly 1012b. In the exemplary embodiment, the blade assemblies 1012a, b each include a plurality of blades 1016a-d that are individually rotationally connected to their respective blade assembly. The first blade assembly 1012a includes a first blade 1016a and a second blade 1016b. The second blade assembly 1012b includes a third blade 1016c and a fourth blade 1016d. The first blade assembly 1012a may be interconnected to the second blade assembly 1012b by a first rack 1014a and the first blade assembly 1012a may be movable along the first rack 1014a relative to the second blade assembly 1012b. A second rack 1014b may also connect the first blade assembly 1012a to the second blade assembly 1012b and the second blade assembly 1012b may be movable along the second rack 1014b relative to the first blade assembly 1012a.

In this alternate embodiment, the blade assemblies 1012 are movable along the racks 1014 in a translational direction allowing for selective expansion of the access channel 1020 along one axis, e.g., the axis of the racks. A mechanism for selecting the position of the blade assemblies 1012 along the racks 1014 may be provided and, in the illustrated embodiment, the mechanism includes a gear assembly 1019. The gear of the gear assembly 1019 is positioned in the first blade assembly 1012a and engages with teeth 1018 provided along the first rack 1014a to move the first blade assembly away from the second blade assembly along the first rack 1014a. The teeth 1018 may extend over the length of the entire first rack 1014a or just a portion of the length. In certain alternate embodiments, a second gear assembly may be provided in the second blade assembly 1012b to engage teeth provided on the second rack 1014b. In the illustrated embodiment, however, a second gear is not provided and the second rack does not include teeth. The gear of the gear assembly 1019 may be accessible from the proximal surface of the first blade assembly 1012a and may have an internal or external drive feature for engagement with an instrument to drive the gear or a handle to drive the gear without a tool. In certain alternate embodiments, in addition to the first gear, a second gear may be provided within the gear assembly 1019. The second gear may be engaged to move the first blade assembly 1012a towards the second blade assembly 1012b along the first rack 1014a.

The position of the blade assemblies 1012 may be locked with respect to the racks 1014 by a spring loaded pawl 1056 which is biased to allow motion in one direction, e.g., expansion but engages the teeth 1018b on rack 1014b, to lock the retractor in a selected expanded position. The pawl 1056 may be disengaged from the teeth 1018b by pressure applied by the user. In an alternate embodiment, the rack 1014b may not have teeth, but rather the pawl 1056 may frictionally engage the rack 1014b.

One skilled in the art will recognize that other mechanisms for selectively advancing the blade assemblies with respect to the rack may be employed including a screw based mechanism whereby a threaded rod is used as the rack or a push button release mechanism for discrete expansion of the blade assemblies.

Figure 17:
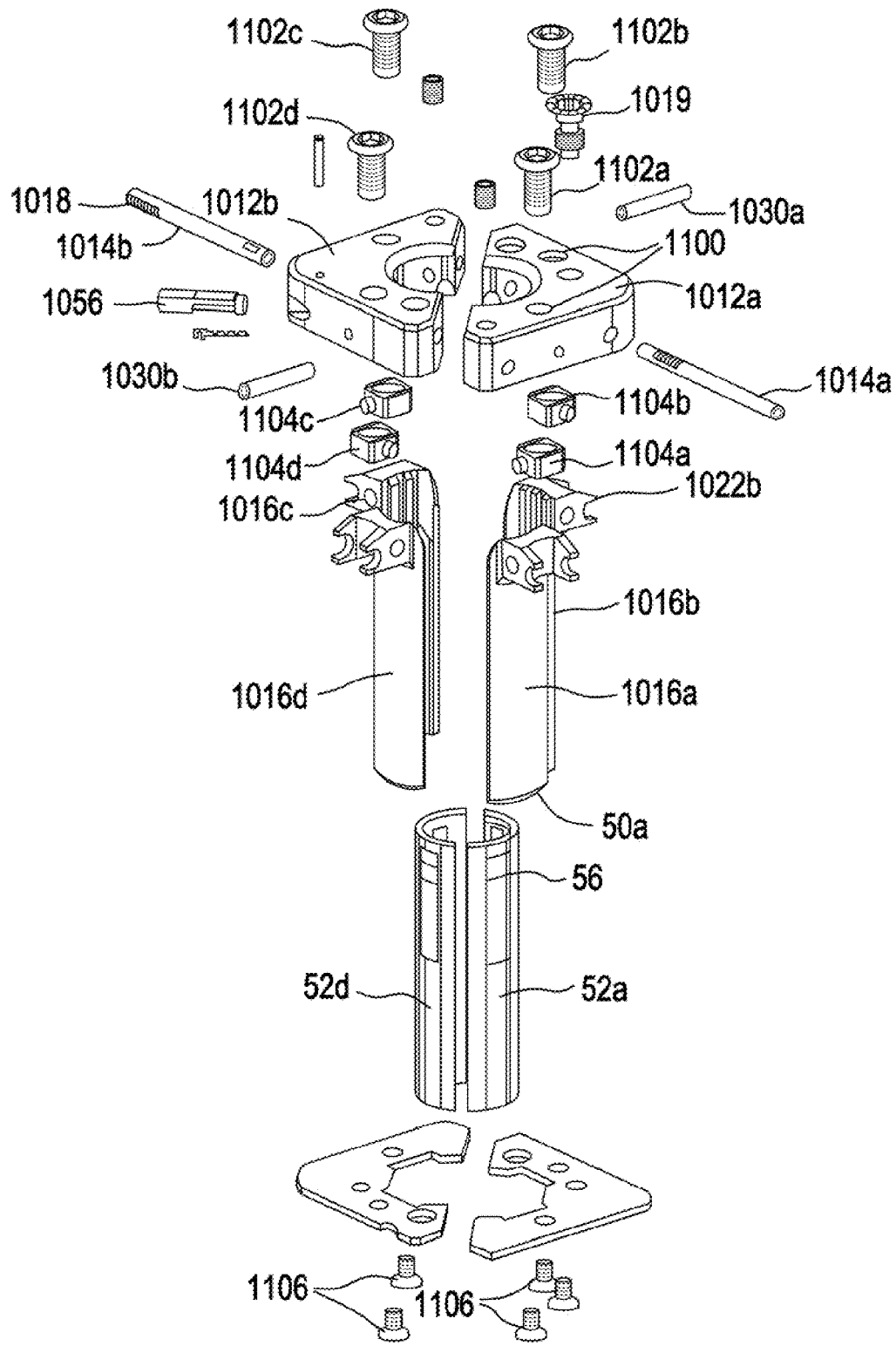
FIG. 17 is an exploded view of the retractor in FIG. 14.
Figure 19:
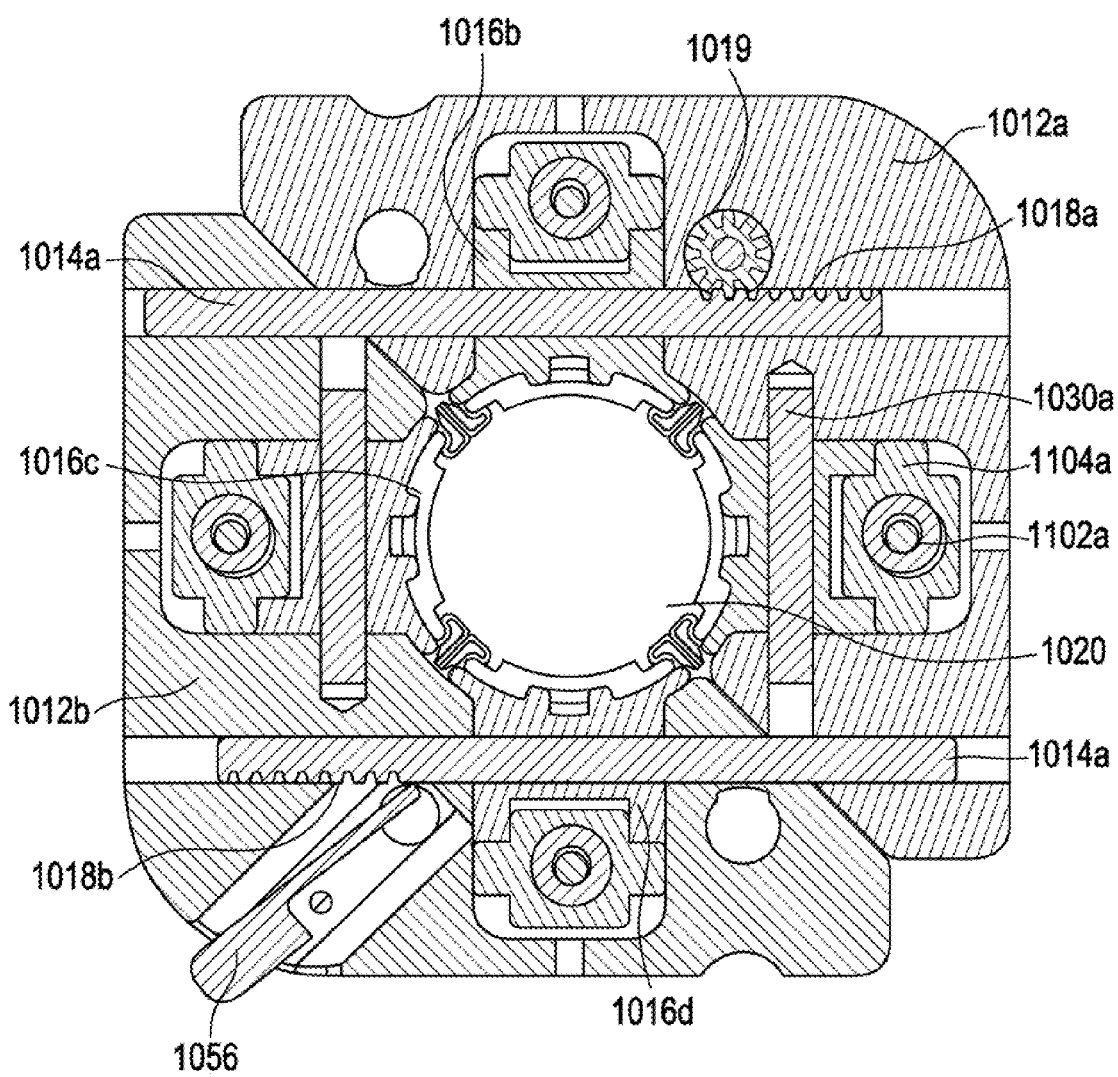
FIG. 19 is a top view in cross-section of the retractor of FIG. 14.

In the closed position of the retractor 1000, the racks 1014 are contained within the blade assemblies 1012a-b. The racks 1014 are exposed between the blade assemblies 1012a-b during expansion of the retractor. The racks 1014a-b may also provide for independent rotational adjustment of at least one blade 1016a-d on each blade assembly 1012a-b. Referring to FIGS. 17 and 19, second blade 1016b and fourth blade 1016d each may be rotationally connected to the respective racks 1014a and 1014b relative to the blade assemblies 1012a-b. In the illustrated embodiment, the proximal end 1022 of each blade 1016 can be configured to provide for rotation of the blade relative to the blade assembly 1012. First blade 1016a and third blade 1016c are individually and rotationally connected to their respective blade assemblies by rods 1030a-b.

As described above, different embodiments of the blade adjustment mechanism maybe used for each blade or all may be the same. Additional exemplary blade adjustment mechanisms are disclosed in U.S. patent application Ser. No. 11/325,621, which is incorporated herein by reference. In the exemplary embodiment, the blade adjustment mechanism is a screw 1102 extending through an opening 1100 in the top surface of the blade assembly 1012 and received within an internally threaded bushing 1104 connected to the blade 1016. The exemplary screw 1102a is cannulated at the distal end of the screw 1102a. A bolt 1106a positioned through an opening in the bottom surface of the blade assembly 1012 is positioned within the cannulated distal end of the screw 1102a to inhibit movement of the screw 1102a off of a screw axis 1108a that is oriented approximately perpendicular to the plane defined by the bottom surface 1116 of the blade assembly 1012. Rotation of the screw 1102a in a first direction causes the first blade 1016a to rotate about rod 1030a from a first, closed position, illustrated in FIG. 15, toward a second, fully expanded position, illustrated in FIG. 21. Rotation of the screw 1102a in a second direction, opposite the first direction, causes the first blade 1012a to rotate about rod 1130a from an expanded position toward the closed position. The same instrument used to drive the gear mechanism to move the blade assemblies along the rack may drive the screw 1102a to rotate the blade relative to the blade assembly.

The blade assemblies 1012a, b may additionally include features for attaching a rigid arm and/or a light source.

One or more of the blades of the retractor may have an adjustable length, e.g. the blade may telescope to selectively adjust the length of the blade. Referring to the exemplary embodiment illustration in FIGS. 1-8, and 14-20 for example, one or more of the blades 16, 1016 may include a primary blade 50 connected to a blade assembly 12 and an adjustable blade 52 that is operatively coupled to the primary blade 50 and is adjustable relative to the primary blade 50 along the length of the primary blade 50. In the exemplary embodiment, blades 16a-d, 1016a-d are adjustable in length and include a respective primary blade 50a-d and a respective adjustable blade 52a-d. Exemplary tissue engaging blades having an adjustable length are disclosed in U.S. Patent Application Publication No. 2005-0137461 A1, which is incorporated herein by reference. The telescoping blades may include a mechanism for selectively adjusting the position of the adjustable blade 52 relative to the primary blade 50. For example, the primary blade 50 may include a plurality of teeth 54 extending along the longitudinal axis of the primary blade 50 and the adjustable blade 52 may include a flexible tab 56 for engaging the teeth 54 of the primary blade 50. The retractor may be inserted through an incision with the adjustable blades 52 in place, as in the case of the exemplary retractor 10 illustrated in FIGS. 1-8 and retractor 1000 illustrated in FIGS. 14-20. Alternatively, the retractor may be inserted through an incision without the adjustable blades in place. In such embodiments, the retractor 10, 1000 may be inserted with the primary blades 50 and one or more adjustable blades may be added after insertion.

The components of the retractors disclosed herein may be manufactured from any biocompatible material including metals, such as stainless steel or titanium, polymers, or composite materials. The components, such as the blades and the frame, may be constructed from the same or different materials.

An exemplary method of providing minimally invasive access to spinal anatomy employing a retractor disclosed herein may include making a skin incision for insertion of the retractor. The incision initially may be less that the diameter of the retractor in the closed configuration (e.g., with the blades of the device in the first, closed position). The incision may be expanded to accommodate the retractor by dilation, for example, by placing one or more dilators through the incision to expand the incision in a stepwise manner. The dilators may be employed to separate or dissect the underlying tissue to the target spinal anatomy. Alternatively, the surgeon may employ his finger or the retractor to dissect the underlying tissue and to expand the initial incision.

Figure 7:
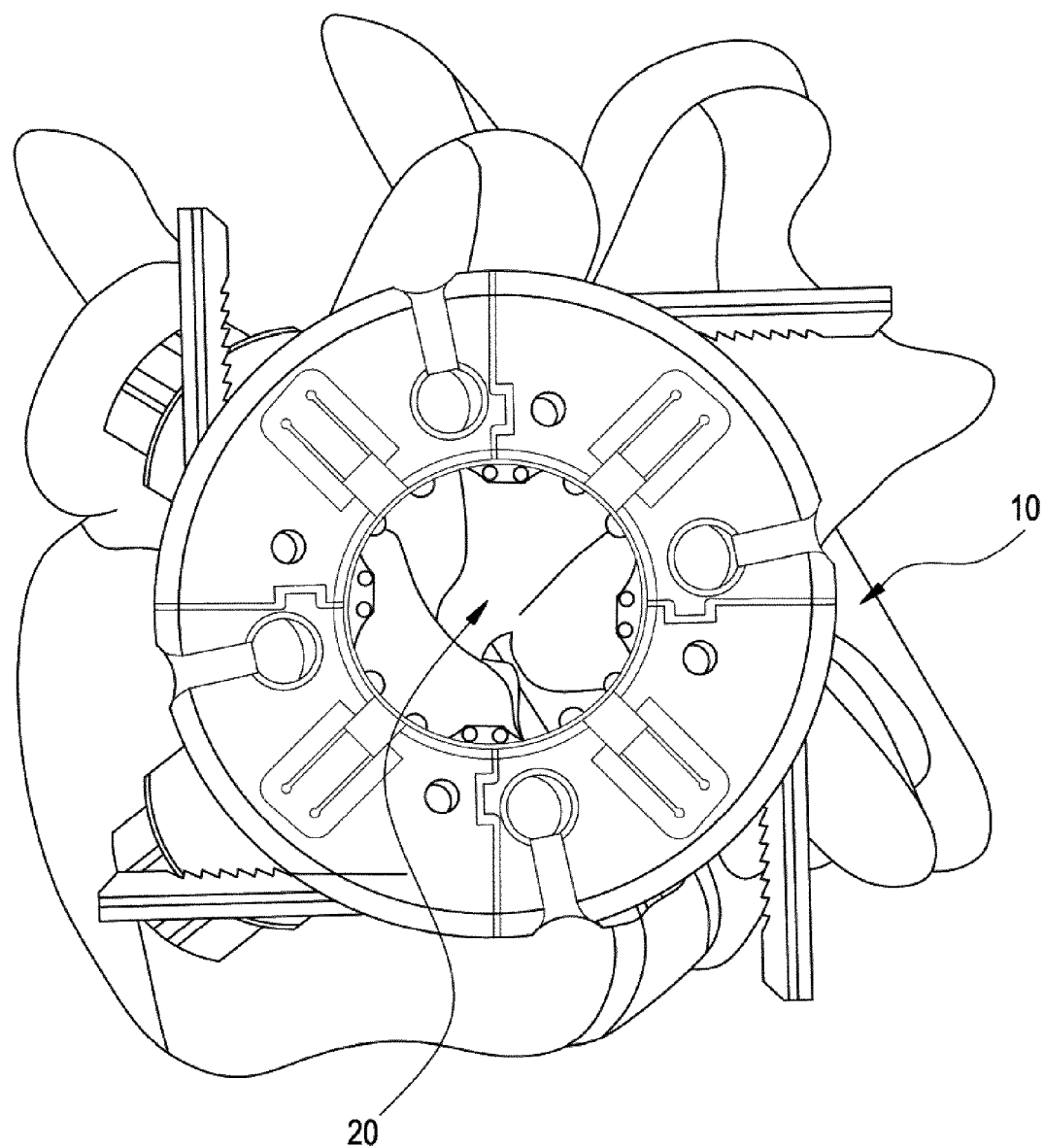
FIG. 7 is a top view of the retractor of FIG. 1, illustrating the retractor in an expanded configuration and positioned to provide access to spinal anatomy in a posterior approach.
Figure 8:
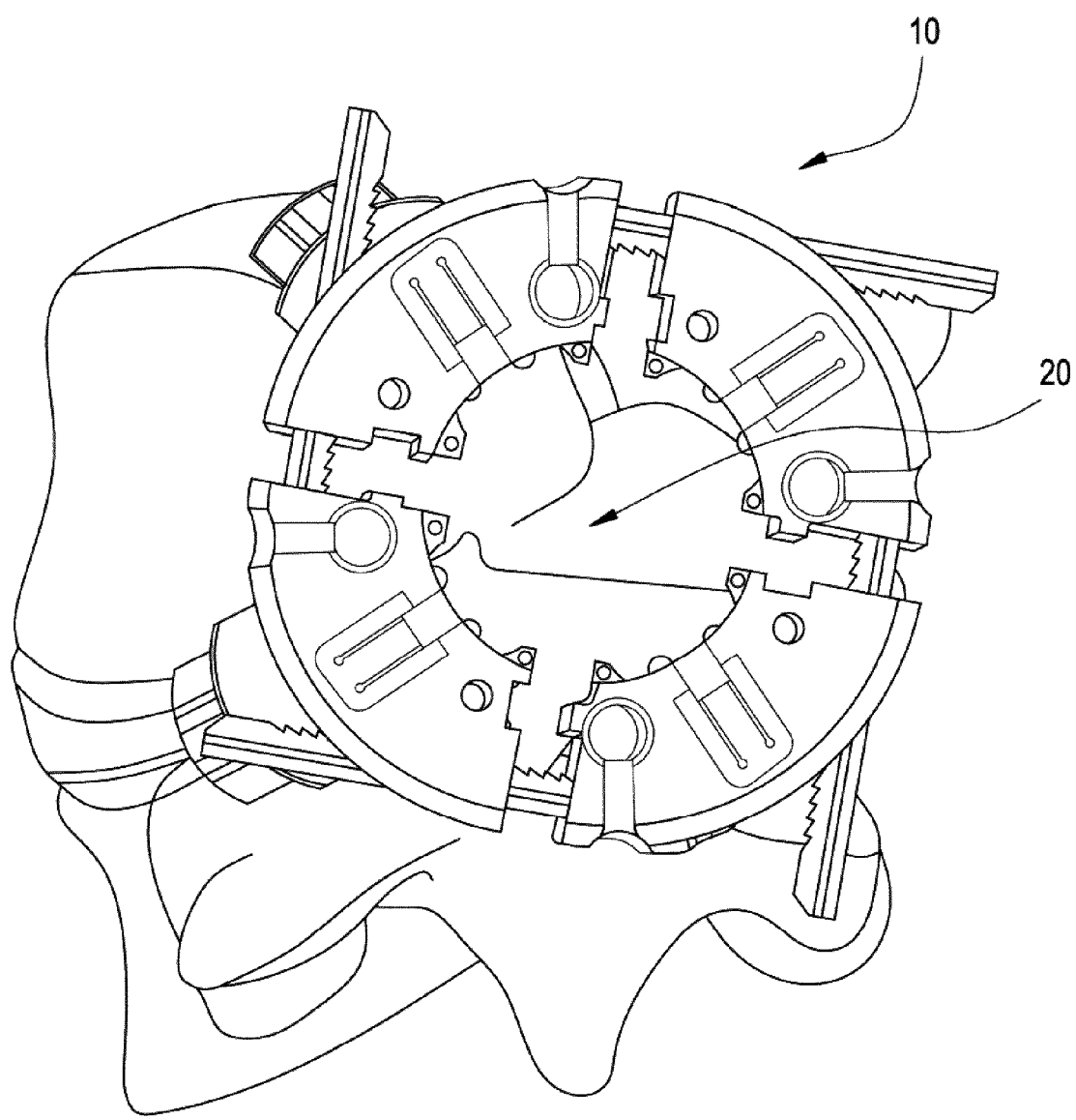
FIG. 8 is a top view of the retractor of FIG. 1, illustrating the retractor in an expanded configuration and positioned to provide access to spinal anatomy in a posterior approach.
Figure 20:
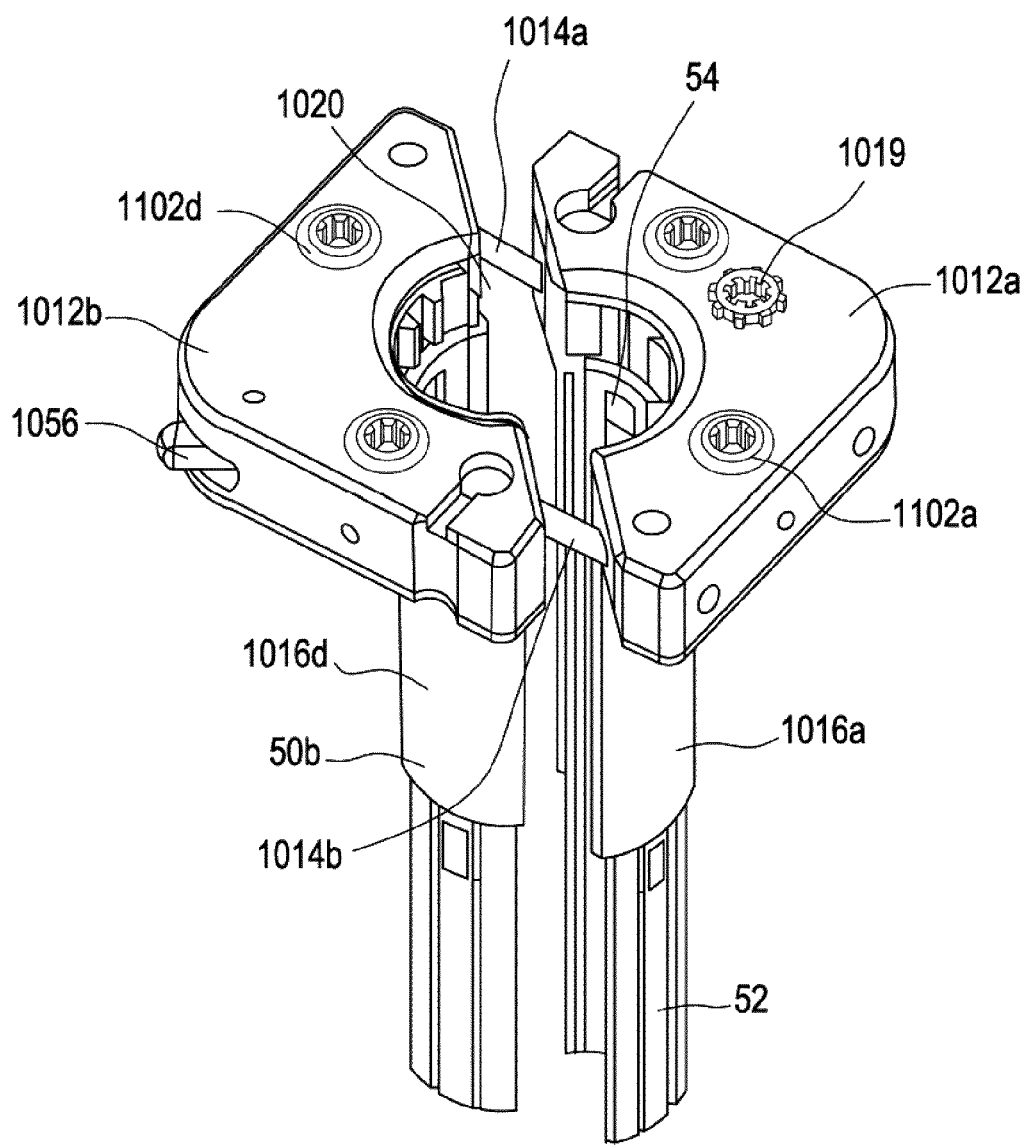
FIG. 20 is a perspective view of the retractor of FIG. 14, illustrating the retractor in an expanded configuration, with the blades in a first closed position and extended.
Figure 21:
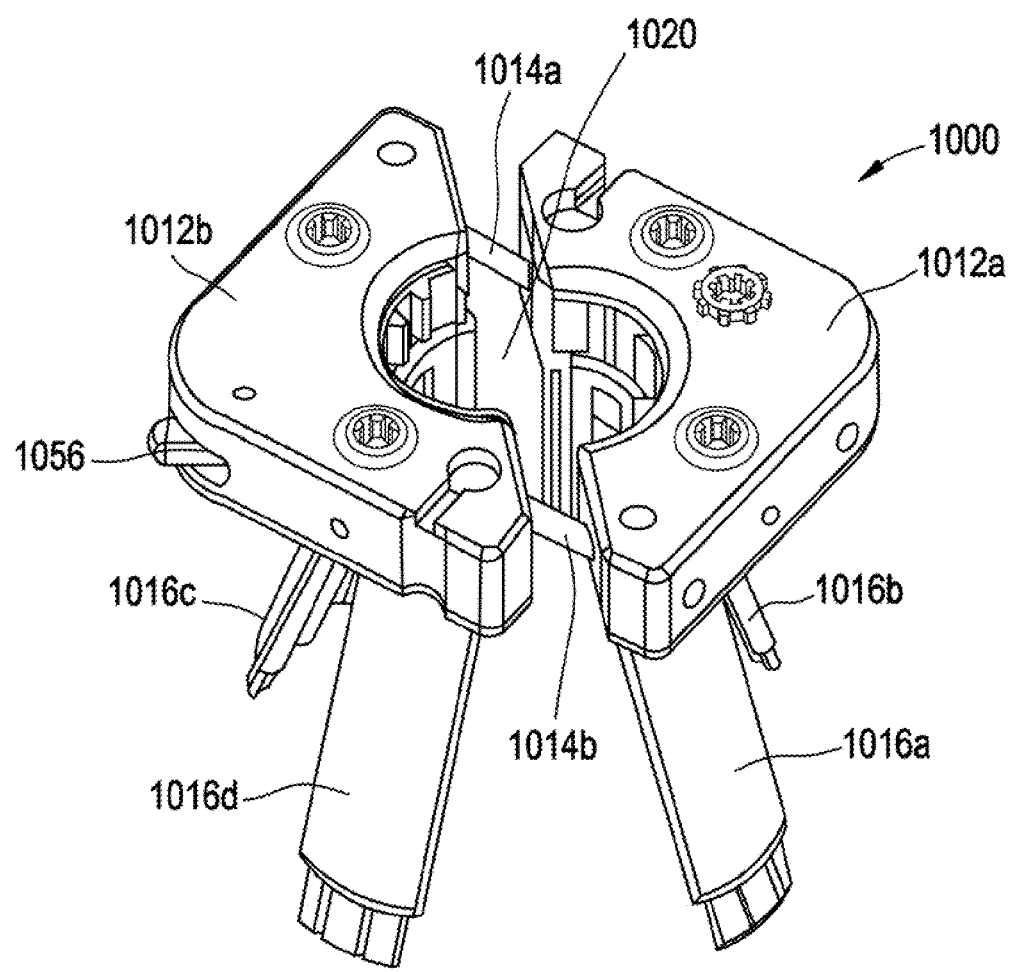
FIG. 21 is a perspective view of the retractor of FIG. 14, illustrating the retractor in an expanded configuration, with the blades in a second expanded position.
Figure 22:
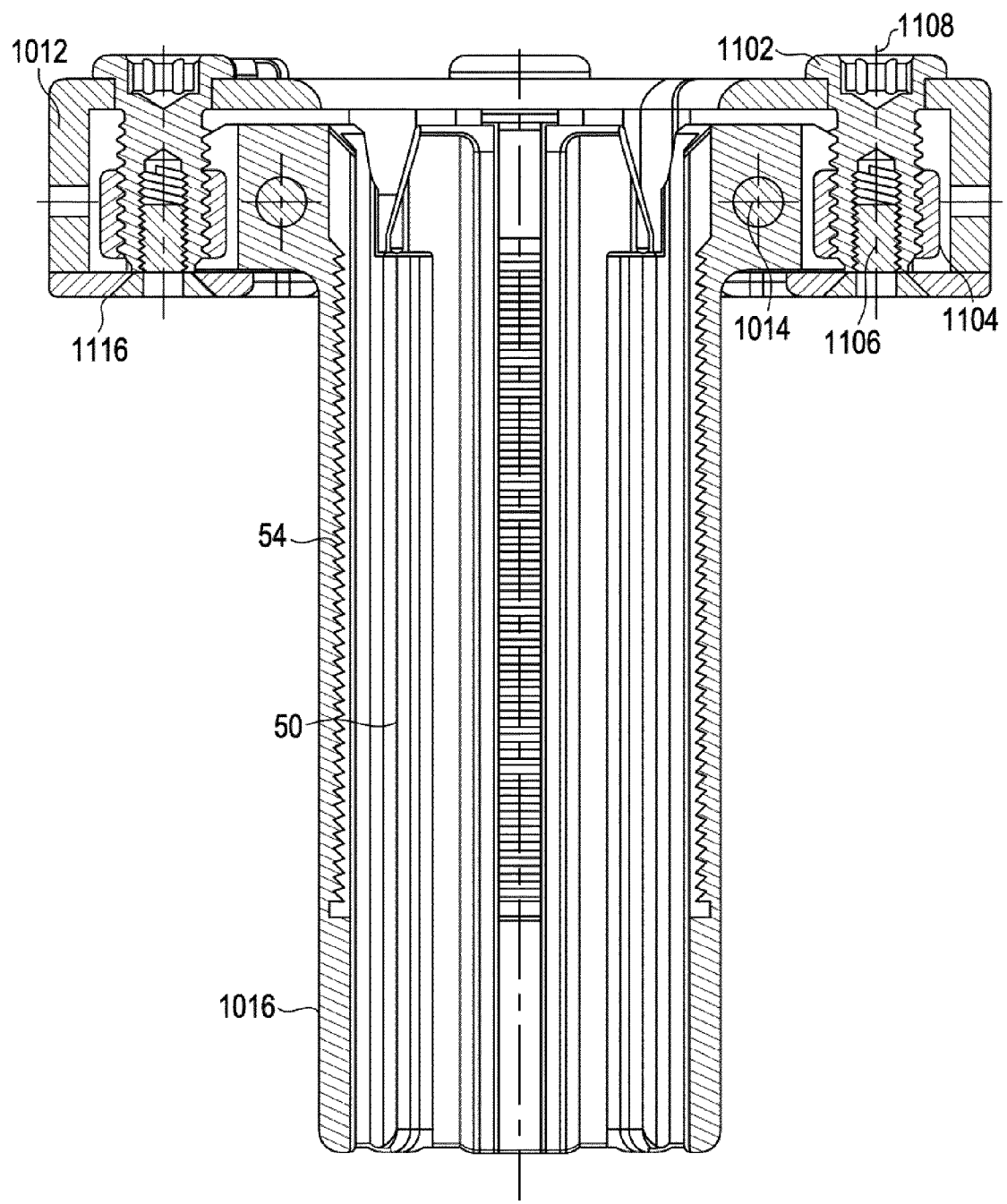
FIG. 22 is a side view in cross-section of the retractor of FIG. 14 in a closed configuration.
Figure 23:
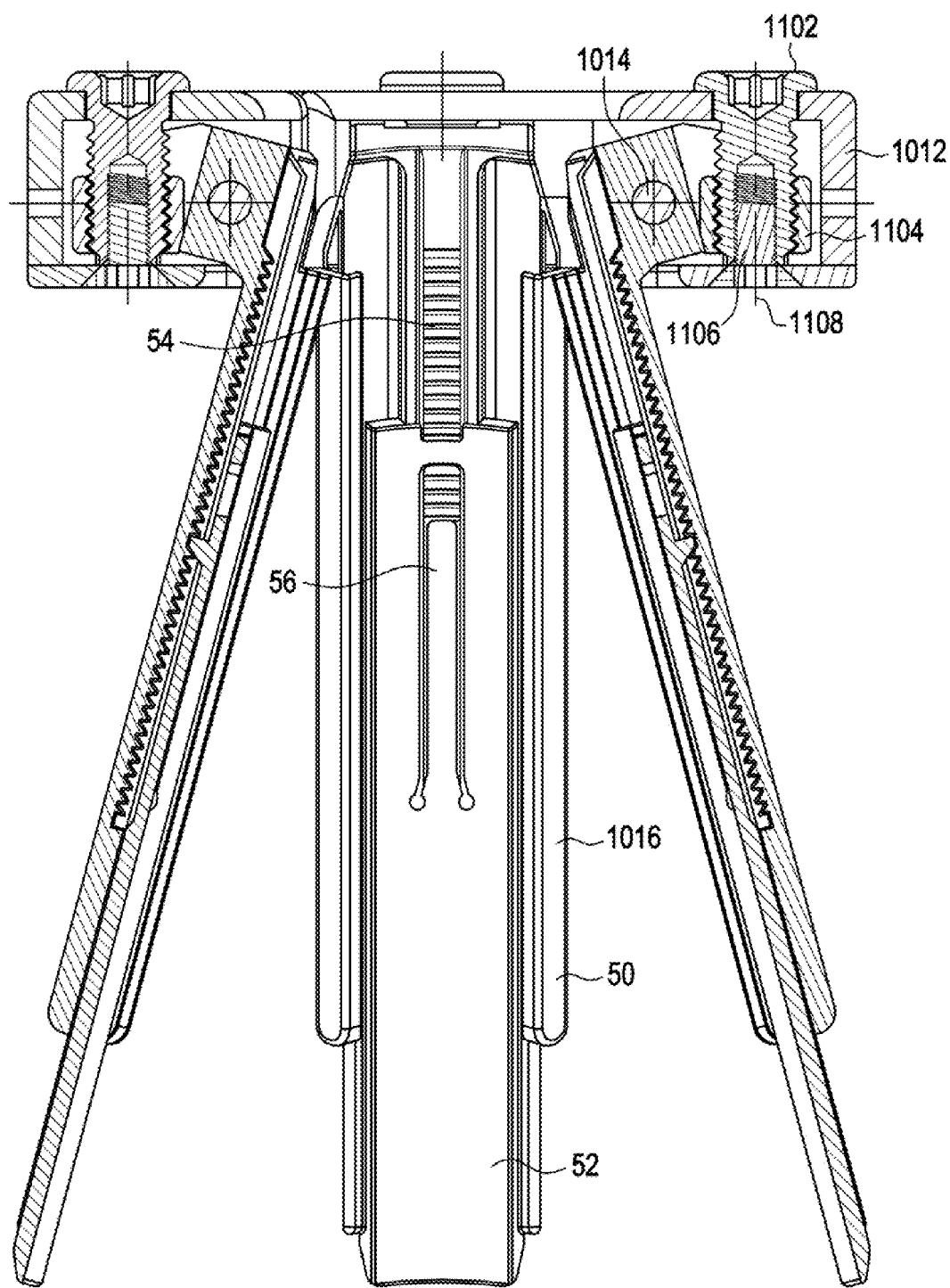
FIG. 23 is a side view in cross-section of the retractor of FIG. 14 in an expanded configuration and with the blades extended.
Figure 24:
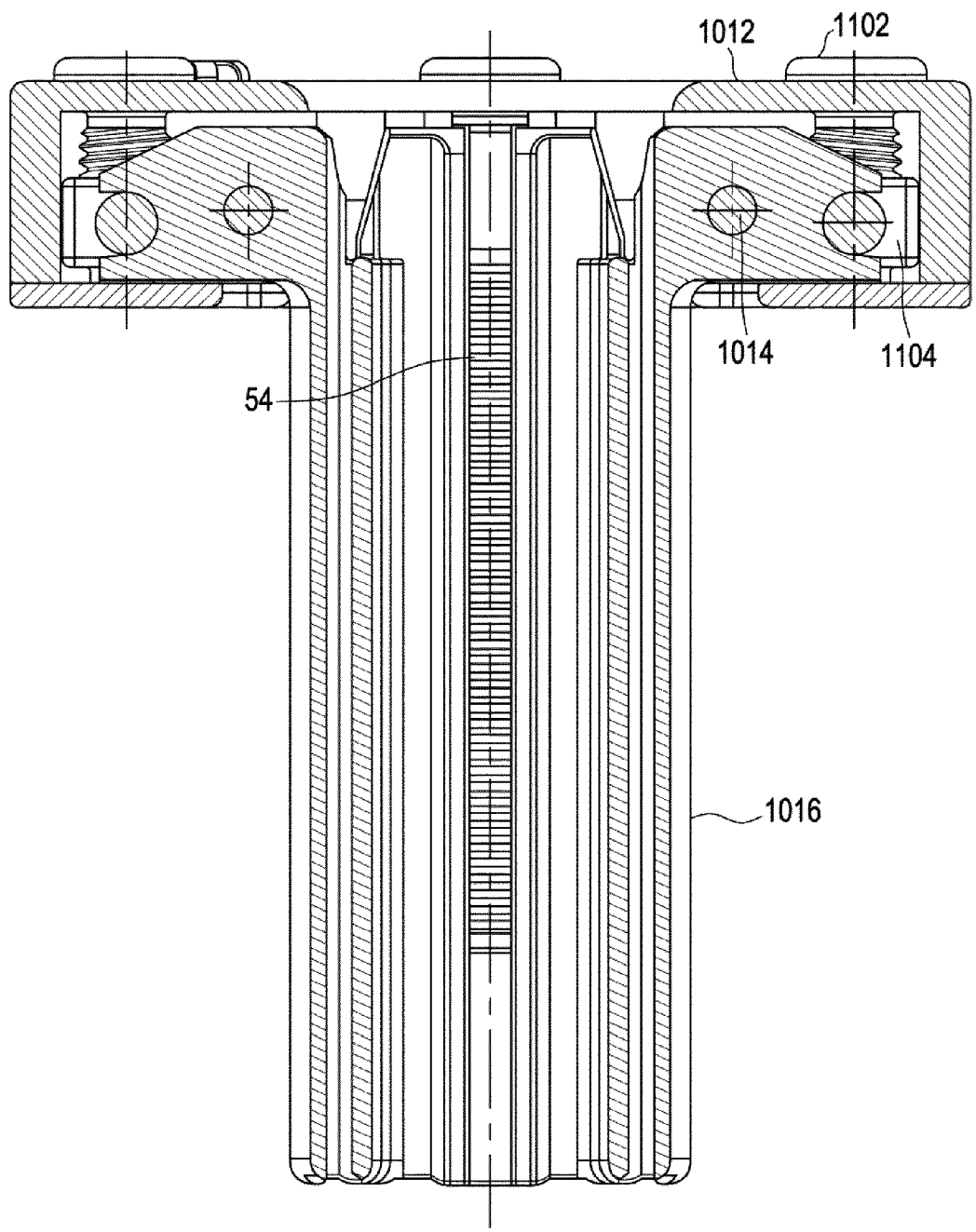
FIG. 24 is an off-set side view in cross-section of the retractor of FIG. 14 in a closed configuration.

The blades of a retractor may be inserted through the incision and the distal ends of the blades may be advanced into proximity to the spinal anatomy. The blades are preferably advanced in a first, closed position, in which the blades are proximate to or contact each other to form a continuously approximately enclosed access channel between the frame, which may be located at the surface of the skin, and the distal ends of the blades. One or more of the blade assemblies may be displaced from the other blade assemblies by moving the blade assembly along a respective rack and thereby expanding the access channel. One or more of the blades may be rotated, using a blade adjustment mechanism, independent of the other blades, to selectively expand the access channel. In the case of the exemplary retractor 10, rotational adjustment of some or all of the blades of the device expands the access channel, particularly at the distal end of the access channel, thereby creating greater working space at proximate the target spinal anatomy. In addition, the length of the working channel may be increased by advancing an adjustable blade of one of the plurality of blades relative to a primary blade along a longitudinal axis of the primary blade. FIG. 7 illustrates exemplary retractor 10 in an expanded configuration in which the blades have been rotated and the retractor 10 has been positioned to provide access to spinal anatomy through a posterior approach. FIG. 8 illustrates the exemplary retractor 10 in an expanded configuration in which the blade assemblies have been displaced from one another along the racks, the blades have been rotated, and the adjustable blades have been displaced relative to the primary blades to expand the access channel. FIG. 18 illustrates an alternate embodiment of a retractor 1000 in which the blade assemblies are in an expanded configuration and the blades have been rotated and the retractor 1000 has been positioned to provide access to the spinal anatomy through a posterior approach. FIG. 20 illustrates the retractor 1000 with the blade assemblies in an expanded configuration and the adjustable blades have been displaced relative to the primary blades. One instrument may be used to displace a blade assembly by moving the blade assembly along a respective rack and thereby expanding the access channel and to rotate one or more of the blades, using a blade adjustment mechanism, independent of the other blades, to selectively expand the access channel.

Any number of surgical procedures may be performed through the access channel including, for example, removal of some or all of one or more discs, placement of bone fusion promoting material, placement of an spine arthroplasty device such as an artificial disc, placement of spinal implants such as hooks, rods, and screws.

After the surgical procedure is performed, the retractor may be returned to the closed configuration and removed from the incision.

While the surgical retractors and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A refractor comprising:
a first blade assembly defining a first housing having a top surface, a bottom surface, a first side surface connecting the top surface and the bottom surface, and a second side surface connecting the top surface and the bottom surface, the first side surface intersecting and oriented perpendicular to the second side surface, the first housing having a first opening between the top surface and the bottom surface and second opening between the top surface and the bottom surface and spaced apart from the first opening, the first opening opposite the first side surface and the second opening opposite the second side surface, the first blade assembly having a first blade having a proximal end and a distal end, the proximal end of the first blade including a rotation opening, the proximal end of the first blade including the rotation opening positioned within the first housing, the first blade extending through the first opening in the first housing such that the distal end of the first blade is positioned outside of the first housing, the first blade assembly including a second blade having a proximal end and a distal end, the proximal end of the second blade including a rotation opening, the proximal end of the second blade including the rotation opening positioned within the first housing, the second blade extending through the second opening in the first housing such that the distal end of the second blade is positioned outside of the first housing; and a second blade assembly defining a second housing having a top surface, a bottom surface, a first side surface connecting the top surface and the bottom surface, and a second side surface connecting the top surface and the bottom surface, the first side surface intersecting and oriented perpendicular to the second side surface, the second housing having a first opening between the top surface and the bottom surface and second opening between the top surface and the bottom surface spaced apart from the first opening, the first opening opposite the first side surface and the second opening opposite the second side surface, the second blade assembly having a third blade having a proximal end and a distal end, the proximal end of the third blade including a rotation opening, the proximal end of the third blade including the rotation opening positioned within the second housing, the third blade extending through the first opening in the second housing such that the distal end of the third blade is positioned outside of the second housing, the second blade assembly including a fourth blade having a proximal end and a distal end, the proximal end of the fourth blade including a rotation opening, the proximal end of the fourth blade including the rotation opening positioned within the second housing, the fourth blade extending through the second opening in the second housing such that the distal end of the fourth blade is positioned outside of the second housing connected thereto, a first rack connecting the first blade assembly and the second blade assembly, a first end of the first rack positioned in the first housing and a second end of the first rack positioned in the second housing, at least one of the first blade assembly and the second blade assembly being movable along the first rack, a second rack connecting the first blade assembly and the second blade assembly, a first end of the second rack positioned in the first housing and a second end of the second rack positioned in the second housing, at least one of the first blade assembly and the second blade assembly being movable along the second rack, the retractor being adjustable between a closed configuration in which the first blade assembly and second blade assembly are proximate one another at least the proximal end thereof and an expanded configuration in which the first blade assembly and the second blade assembly are displaced from another and wherein the first rack extends through the rotation opening of the first blade, the first blade being rotatable about the first rack, and the second rack extends through the rotation opening of the third blade, the third blade being rotatable about the second rack.

2. The retractor of claim 1, wherein the first blade is rotatably connected to the first blade assembly and is rotatable independent of the second blade relative to the first blade assembly, and the third blade is rotatably connected to the second blade assembly and is rotatable independent of the fourth blade relative to the second blade assembly.

3. The retractor of claim 1, wherein, the first blade is rotatably connected to the first blade assembly and is rotatable independent of the second blade relative to the first blade assembly, and the fourth blade is rotatably connected to the second blade assembly and is rotatable independent of the third blade relative to the second blade assembly.

4. The retractor of claim 1, wherein, the second blade is rotatably connected to the first blade assembly and is rotatable independently of the first blade relative to the first blade assembly, and the third blade is rotatably connected to the second blade assembly and is rotatable independent of the fourth blade relative to the second blade assembly.

5. The retractor of claim 1, wherein, the second blade is rotatably connected to the first blade assembly and is rotatable independently of the first blade relative to the first blade assembly, and the fourth blade is rotatably connected to the second blade assembly and is rotatable independent of the third blade relative to the second blade assembly.

6. The retractor of claim 1, wherein, the first blade is rotatably connected to the first blade assembly and is rotatable independent of the second, third, and fourth blades.

7. The retractor of claim 1, wherein, the second blade is rotatably connected to the first blade assembly and is rotatable independent of the first, third and fourth blades.

8. The retractor of claim 1, wherein the third blade is rotatably connected to the second blade assembly and is rotatable independent of the first, second, and fourth blades.

9. The retractor of claim 1, wherein, the fourth blade is rotatably connected to the second blade assembly and is rotatable independent of the first, second and third blades.

10. The retractor of claim 1, wherein the blades contact adjacent blades along a length of the blades to form a continuously enclosed working channel when the retractor is in the closed configuration.

11. The retractor of claim 10, wherein the working channel has an approximately circular cross section when the retractor is in the closed configuration.

12. The retractor of claim 1 wherein the first and second racks are contained within the first and second blade assemblies.

13. The retractor of claim 1, wherein the retractor is adjustable to a fully expanded configuration in which the first blade assembly and the second blade assembly are fully displaced from one another.

14. The retractor of claim 1 further comprising, a gear positioned in the first housing of the first blade assembly, the gear engaging the first rack to facilitate movement of the first blade assembly relative to the second blade assembly.

15. The retractor of claim 1, wherein the blades each comprise a primary blade connected to the blade assembly, and an adjustable blade operatively coupled to the primary blade and adjustable relative to the primary blade along a longitudinal axis of the primary blade.

16. The retractor of claim 1, further comprising: a first blade adjustment mechanism for selectively adjusting the rotational position of the first blade and a third blade adjustment mechanism for selectively adjusting the rotational position of the third blade.

* * * * *